(12) United States Patent
Popplewell et al.

(10) Patent No.: US 11,106,773 B2
(45) Date of Patent: Aug. 31, 2021

(54) SYSTEM AND METHOD FOR AN IMPROVED PERSONAL VAPORIZATION DEVICE

(71) Applicant: CANOPY GROWTH CORPORATION, Smiths Falls (CA)

(72) Inventors: Peter Popplewell, Ottawa (CA); Andrew Stewart, Ottawa (CA); Steven Penney, Ottawa (CA)

(73) Assignee: CANOPY GROWTH CORPORATION, Smiths Falls (CA)

( * ) Notice: Subject to any disclaimer, the term of this patent is extended or adjusted under 35 U.S.C. 154(b) by 233 days.

(21) Appl. No.: 16/419,593

(22) Filed: May 22, 2019

(65) Prior Publication Data

US 2019/0272359 A1    Sep. 5, 2019

Related U.S. Application Data

(63) Continuation-in-part of application No. 15/921,144, filed on Mar. 14, 2018, now Pat. No. 10,327,479, and
(Continued)

(51) Int. Cl.
*A24F 47/00* (2020.01)
*G06F 21/32* (2013.01)
(Continued)

(52) U.S. Cl.
CPC .............. *G06F 21/32* (2013.01); *A24F 40/53* (2020.01); *A24F 40/65* (2020.01); *A61M 15/06* (2013.01);
(Continued)

(58) Field of Classification Search
CPC ........... A24F 40/50; A24F 40/53; A24F 40/65
See application file for complete search history.

(56) References Cited

U.S. PATENT DOCUMENTS

| 8,897,628 B2 | 11/2014 | Conley et al. |
| 9,155,337 B2 | 10/2015 | Duncan et al. |

(Continued)

FOREIGN PATENT DOCUMENTS

| WO | 2017144374 A1 | 8/2017 |
| WO | 2017205692 A1 | 11/2017 |

OTHER PUBLICATIONS

International Search Report and Written Opinion issued in PCT/CA2018/050310, dated Mar. 14, 2018, 15 pages.
(Continued)

*Primary Examiner* — Eric Yaary
(74) *Attorney, Agent, or Firm* — Stinson LLP

(57) ABSTRACT

A vape device system including a payload reservoir that is identified by a payload identifier and that is configured to hold a substance for atomization. A processor is configured to determine an operational setting based on at least one of the payload identifier and a secondary data, which may include user information, prescription information, location information, payload information, historical vape device usage information, and historical payload reservoir information. A vape device system, and method of using the same, that includes a vape device and a computing device that includes the processor. A method of controlling a vape device including determining an operational setting of the vape device based on the payload identifier and/or secondary data. The operational settings may include a duty cycle setting, a temperature setting, an operational time duration, a dosage setting, and a security setting.

39 Claims, 4 Drawing Sheets

Related U.S. Application Data a continuation-in-part of application No. PCT/CA2019/050316, filed on Mar. 14, 2019, which is a continuation-in-part of application No. 15/921,144, filed on Mar. 14, 2018, now Pat. No. 10,327,479.

(60) Provisional application No. 62/471,751, filed on Mar. 15, 2017, provisional application No. 62/733,286, filed on Sep. 19, 2018.

(51) Int. Cl.
| | | |
|---|---|---|
| *G06F 21/31* | (2013.01) | |
| *A61M 15/06* | (2006.01) | |
| *A24F 40/53* | (2020.01) | |
| *A24F 40/65* | (2020.01) | |
| *A24F 40/10* | (2020.01) | |
| *A24F 40/49* | (2020.01) | |

(52) U.S. Cl.
CPC .............. *G06F 21/31* (2013.01); *A24F 40/10* (2020.01); *A24F 40/49* (2020.01); *A61M 2205/123* (2013.01); *A61M 2205/6009* (2013.01)

(56) References Cited

U.S. PATENT DOCUMENTS

| | | |
|---|---|---|
| 9,770,055 B2 | 9/2017 | Cameron et al. |
| 10,201,185 B2 | 2/2019 | Bleloch et al. |
| 10,327,479 B2 | 6/2019 | Popplewell et al. |
| 2013/0284192 A1 | 10/2013 | Peleg et al. |
| 2014/0096782 A1 | 4/2014 | Ampolini et al. |
| 2014/0107815 A1 | 4/2014 | LaMothe |
| 2015/0122252 A1 | 5/2015 | Frija |
| 2015/0136158 A1 | 5/2015 | Stevens et al. |
| 2015/0181945 A1* | 7/2015 | Tremblay ................ A24F 40/60 131/328 |
| 2015/0208731 A1 | 7/2015 | Malamud et al. |
| 2015/0237917 A1 | 8/2015 | Lord |
| 2016/0106936 A1 | 4/2016 | Kimmel |
| 2016/0242466 A1 | 8/2016 | Lord et al. |
| 2017/0231284 A1 | 8/2017 | Newns |
| 2017/0258136 A1 | 9/2017 | Hawes et al. |
| 2018/0043114 A1 | 2/2018 | Bowen et al. |
| 2018/0060873 A1 | 3/2018 | Chu |
| 2018/0177231 A1 | 6/2018 | Woodbine et al. |

OTHER PUBLICATIONS

International Search Report and Written Opinion issued in PCT/CA2019/050316, dated May 1, 2019, 15 pages.

Petition for Post-Grant Review of related U.S. Pat. No. 10,327,479, Case No. PGR2020-00044, dated Mar. 23, 2020 (84 pgs).

Exhibit 1013 to Petition for Post-Grant Review of related U.S. Pat. No. 10,327,479 B2, Claim Chart for Invalidity of U.S. Pat. No. 10,327,479, Mar. 23, 2020 (20 pgs).

Exhibit 1014 to Petition for Post-Grant Review of related U.S. Pat. No. 10,327,479 B2, Declaration of Joe Keenan Regarding Petition for Post-Grant Review, Mar. 23, 2020 (8 pgs).

Exhibit JFK-1 to Declaration of Joe Keenan, filed in Petition for Post-Grant Review of related U.S. Pat. No. 10,327,479 B2, Resume' of Joe Keenan, Mar. 23, 2020 (8 pgs).

Exhibit 1015 to Petition for Post-Grant Review of related U.S. Pat. No. 10,327,479 B2, Declaration of Dr. Vladislav Babinsky Regarding Petition for Post-Grant Review, Mar. 23, 2020 (120 pgs).

Exhibit JFK-2 to Declaration of Joe Keenan, filed in Petition for Post-Grant Review of related U.S. Pat. No. 10,327,479 B2, Press Release, "Microchip Introduces New Unique ID Family of EEPROMs", Jun. 5, 2013 (3 pgs).

Exhibit JFK-3 to Declaration of Joe Keenan, filed in Petition for Post-Grant Review of related U.S. Pat. No. 10,327,479 B2, Document, "Medical Device Tracking Guidance for Industry and Food and Drug Administration Staff", The Food and Drug Administration (FDA), Mar. 27, 2014 (13 pgs).

Exhibit JFK-4 to Declaration of Joe Keenan, filed in Petition for Post-Grant Review of related U.S. Pat. No. 10,327,479 B2, Document, "Drug Supply Chain Security Act (DSCSA)", Nov. 27, 2013 (5 pgs).

Exhibit JFK-5 to Declaration of Joe Keenan, filed in Petition for Post-Grant Review of related U.S. Pat. No. 10,327,479 B2, Document, "What We Do—About GS1", pages were downloaded from the internet on Mar. 17, 2020 (internet address not provided) (3 pgs).

Exhibit JFK-6 to Declaration of Joe Keenan, filed in Petition for Post-Grant Review of related U.S. Pat. No. 10,327,479 B2, Document, "HDA—Pharmaceutical Traceability", pages were downloaded from the internet on Mar. 17, 2020 https://www.hda.org/issues/pharmaceutical-traceability (5 pgs).

Exhibit JFK-7 to Declaration of Joe Keenan, filed in Petition for Post-Grant Review of related U.S. Pat. No. 10,327,479 B2, Document, "ISO/IEC 15459-4:2006 [ISO/IEC 15459-4:2006] Information technology—Unique identifiers for supply chain management", pages were downloaded from the internet on Mar. 17, 2020, https://www.iso.org/standard/43455.html.

Exhibit JFK-8 to Declaration of Joe Keenan, filed in Petition for Post-Grant Review of related U.S. Pat. No. 10,327,479 B2, Document, "Unique Identification 101. The Basics" U.S. Department of Defense, Jun. 2004 (21 pgs).

Exhibit JFK-9 to Declaration of Joe Keenan, filed in Petition for Post-Grant Review of related U.S. Pat. No. 10,327,479 B2, Document, "Use Unique ID EEPROM in Your Embedded System to Prevent Design Counterfeiting", Altium Designer, May 10, 2018 (5 pgs).

Exhibit JFK-10 to Declaration of Joe Keenan, filed in Petition for Post-Grant Review of related U.S. Pat. No. 10,327,479 B2, Product page for "DS2433 4Kb 1-Wire EEPROM", downloaded from the internet on Mar. 12, 2020 at https://maximintegrated.com/en/products/ibutton-one-wire/memory-products/DS2433.html (4 pgs).

Exhibit JFK-11 to Declaration of Joe Keenan, filed in Petition for Post-Grant Review of related U.S. Pat. No. 10,327,479 B2, Product page for "EEPROM Enables Remote Identification", FierceElectronics, downloaded from the internet on Mar. 12, 2020 at https://www.fierceelectronics.com/embedded/eeproom-enables-remote-identification (4 pgs).

Exhibit JFK-12 to Declaration of Joe Keenan, filed in Petition for Post-Grant Review of related U.S. Pat. No. 10,327,479 B2, Press Release, "Latest Single-Wire Serial EEMPROM from Microchip Enables Remote Identification", Microchip, Nov. 8, 2017 (3 pgs).

Exhibit JFK-13 to Declaration of Joe Keenan, filed in Petition for Post-Grant Review of related U.S. Pat. No. 10,327,479 B2, Product Information, "EEPROMs that include a MAC address and/or a unique ID", Microchip, downloaded from the internet on Feb. 27, 2020 at https://www.microchip.com/design-centers/memory/serial-eeproom/mac-address-and-unique-id-eeproms (3 pgs).

Exhibit JFK-14 to Declaration of Joe Keenan, filed in Petition for Post-Grant Review of related U.S. Pat. No. 10,327,479 B2, Product Information, "AT24MAC402. 2Kb I2C compatible 2-wire Serial EEPROM with Pre-programmed EUI-48 MAC Address", Microchip, downloaded from the internet on Mar. 17, 2020 at https://www.microchip.com/wwwproducts/en/AT24MAC402 (3 pgs).

Exhibit JFK-15 to Declaration of Joe Keenan, filed in Petition for Post-Grant Review of related U.S. Pat. No. 10,327,479 B2, Datasheet for "AT21CS01/AT21CS11. Single-Wire, I/O Powered 1Kbit (128 x 8) Serial EEPROM with a Unique, Factory-Programmed 64-Bit Serial Number", Alcom Electronics, Microchip Technology Inc., 2017 (48 pgs).

Exhibit JFK-16 to Declaration of Joe Keenan, filed in Petition for Post-Grant Review of related U.S. Pat. No. 10,327,479 B2, Datasheet for "M24128-A125. Automotive 128-Kbit serial I2C bus EEPROM with 1 MHz clock", life. augmented, Feb. 2016 (42 pgs).

Exhibit JFK-17 to Declaration of Joe Keenan, filed in Petition for Post-Grant Review of related U.S. Pat. No. 10,327,479 B2, Product Information, "ATSHA204A-RBHCZ-T Microchip Technology/Integrated Circuits (ICs)/DigiKey", Digi-Key Electronics, downloaded from the internet on Mar. 17, 2020 at https://www.digikey.

(56) References Cited

OTHER PUBLICATIONS com/product-detail/en/microchip-technology/A...s&gclid=EAIaIQobChMIn_WV7eqf6AlVBNvACh10MA76EAQYAyABEgJxtPD_Bwe (4 pgs).

* cited by examiner

SYSTEM AND METHOD FOR AN IMPROVED PERSONAL VAPORIZATION DEVICE

CROSS-REFERENCE TO RELATED APPLICATIONS

This application is a continuation-in-part of and claims priority to U.S. patent application Ser. No. 15/921,144, filed on Mar. 14, 2018, which is based on and claims priority to U.S. Provisional Application Ser. No. 62/471,751, filed on Mar. 15, 2017, each of which is incorporated herein by reference in its entirety.

This application is also a continuation-in-part of and claims priority to International Patent Application No. PCT/CA2019/050316, filed on Mar. 14, 2019, which (i) is a continuation-in-part of and claims priority to U.S. patent application Ser. No. 15/921,144, filed on Mar. 14, 2018, and (ii) is based on and claims priority to U.S. Provisional Application Ser. No. 62/733,286 filed on Sep. 19, 2018, each of which is incorporated herein by reference in its entirety.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

1. Field of the Invention

The present disclosure is related to the field of personal vaporizer devices or "vape devices," and in particular, methods and systems for controlling the operation of vape devices.

2. Description of Related Art

The use of personal vaporizers or vape devices for consuming tobacco products, as well as cannabis for medical and recreational purposes, has grown significantly. Many of the vape devices merely contain an atomizer for heating and vaporizing liquids or oils to be inhaled. In a basic form, vape devices can be simple devices consisting of a heating element, a battery, a switch for connecting the battery to the heating element, and an amount of liquid or oil to be vaporized by the heating element. Controlling the vape device merely entails closing the switch to heat the liquid or oil to produce vapor to be inhaled. Conventional vape devices such as these provide: no control as to the ramping up and/or down of power applied to the heating element; no control as to the metering of how much vapor is produced when the switch is closed; no control as to how particular fluids or oils are to be heated to produce vapor; and no control to prevent unauthorized use of the vape device by anyone other than the user of the vape device.

BRIEF SUMMARY OF THE INVENTION

In some embodiments, a high-quality, best-in-class rechargeable vape device is provided. This product is simple and intuitive and appeals instantly to the "cannabis-naive" customer, whether medical or recreational. In some embodiments, the vape device can communicate with a personal computing device and work interactively with an application or "app" operating on the personal computing device to provide additional functions and features that can meet the demands and needs of the most sophisticated connoisseur or medical patient. For the purposes of this description and the claims that follow, the term "personal computing device" is defined as including personal computers, laptop computers, personal digital assistants, personal computing tablets (such as those made by Apple® and Samsung®, and by others as well known to those skilled in the art), smart phones (such as those running on iOS® and Android® operating systems, and others as well known to those skilled in the art), smart watches, fitness tracking wristbands, wearable devices, smart glasses, and any other electronic computing device that comprises means for communications (wireless or wired) with other electronic devices, and with a global telecommunications or computing network.

In some embodiments, the vape device can comprise security settings to prevent unauthorized use of the vape device by anyone other than the owner of the vape device, who has a prescription for medical marijuana. In some embodiments, the security settings can prevent the use of the vape device in regions or jurisdictions, even by the rightful owner of the vape device, where the consumption of medical marijuana is not authorized or legal. These security settings can be implemented to appease government or law enforcement for unauthorized use of the vape device in the consumption of cannabis products, for medical purposes or otherwise.

In some embodiments, the vape device can comprise a disposable or single-use version with reduced functionality but adapted from higher quality embodiments thereof.

In some embodiments, the vape device can comprise a traditional "cigarette appearance" while other embodiments can comprise a non-cigarette appearance.

In some embodiments, the vape device can comprise a light to emulate the ember of a cigarette when vapor is being inhaled.

In some embodiments, the vape device, in combination with an app running on a personal computing device, can control the temperature and/or duty cycle of vaporization to optimize for flavor or vapor quantity for any given type of fluid or oil to be vaporized for inhalation. In some embodiments, the app can be used to improve the efficiency of the operation of the vape device and to maximize the longevity of a fluid or oil-filled cartridge or payload reservoir used in the vape device.

In some embodiments, the app can include features to customize a user's vape device, such as naming the vape device, selecting its color and controlling a vibrating device disposed in the vape device. In some embodiments, the app can include security settings to control access to the vape device, and to lock it when not in use.

In some embodiments, the vape device can comprise a processor operating on firmware disposed thereon. Connectivity between the vape device and the app disposed on the personal computing device can enable means for updating the firmware on the vape device to keep it operating on the most current firmware. In some embodiments, the vape device can comprise a physical configuration that can be adapted to display an OEM brand or sub-brand depending on the brand, the sales channel for the branded vape device, and the vape device's anticipated end use such as medical, recreational, etc.

In some embodiments, the vape device will be used with high quality oil products that cannot leak from the vape device. The vape device will avoid producing stale smoke by high temperature heating, quick cooling and providing a fast path for vapor to be inhaled from the vape device.

In some embodiments, the vape device can comprise a battery as a power source for vaporizing oils and liquids. The battery can comprise a lithium ion power cell although other battery technologies can be used, as well known to those skilled in the art. As the vape device is a personal use device, the battery can comprise technology that prevents the advent of an explosion should the battery fail.

In some embodiments, the vape device can be configured not to contain or use propylene glycol ("PG") or other non-essential chemicals anywhere, whether in the oils used in the vape device or on materials used in the manufacture thereof.

In some embodiments, the vape device can comprise means for preventing it from overheating.

In some embodiments, the vape device can comprise means for preventing it from producing latent odors or smells. The vape device can further be configured to produce vapor that can be seen when it is exhaled by a user.

In some embodiments, the vape device can be configured to enable viewing of oils or fluids in a cartridge or payload reservoir when it is inserted into the vape device. In other embodiments, the vape device can be configured so that the oil or fluid in the cartridge is not visible when the cartridge is inserted into the vape device.

In some embodiments, the vape device can be configured to be water-resistant or water-proof.

In some embodiments, cartridges for use with the vape device can be separated from the vape device, and can be available in various sizes in terms of the amount of liquid or oil it can contain.

In some embodiments, each cartridge or payload reservoir can comprise a unique serial number or payload identifier, and the vape device can further comprise means for determining whether the vape device can work with the cartridge or not depending on the specific serial number of the cartridge.

In some embodiments, the vape device can comprise means for acquiring data on a cartridge based on the serial number of the cartridge that can be used to control the operation of the vape device. For example, the vape device can acquire certain data specific to the fluid or oil in the cartridge to know the manufacturer-recommended temperature and/or duty cycle for heating the fluid or oil in order to achieve optimum vaporization. In some embodiments, the vape device can comprise means for enabling the user to alter one or more operational settings of the vape device to suit the user's personal preferences. In some embodiments, the vape device can comprise means for tracking of data relating to the operation of the vape device and its use by a user. In some embodiments, the vape device can be configured to provide warnings in the advent of certain conditions of the vape device, such as when, the cartridge is almost empty, when the battery is nearly depleted, when the heating element is overheating or non-functioning to name but a few. In some embodiments, the vape device can comprise means for monitoring and collecting data on how the vape device is being used by a user, and to provide information and assessments about the way the user uses the vape device in addition to being able to provide advice to the user on how to improve or optimize their use of the vape device based on the user's current use of the vape device.

In some embodiments, the vape device can be configured for exchanging data with other personal computing devices that a user may use or possess, such as a smart phone or device (like an iPhone® or Apple® Watch®) or a fitness tracking wristband (like a Fitbit®) to provide the user with further information on their life and habits.

In some embodiments, the vape device can comprise means for locating it should it become lost. This can include means for communicating with a smart phone or device to provide similar functionality as the Find iPhone™ app as used on Apple® iPhones® and iPads®.

In some embodiments, the vape device can be configured for communicating with an app running on a smart phone or personal computing device, wherein the app can comprise the ability to adjust the temperature and/or duty cycle the heating element operates at, as well as being able to control the operation of the vape device for users of various experience. As an example, the app can enable an anti-cough setting on the vape device for a novice user.

A personal vaporizer device or "vape device" that can communicate with smart phones or devices and operate in conjunction with applications running thereon to control and monitor the use of the vape device by a user.

In some embodiments, the app can be configured to acquire specific information on the liquid or oil being vaporized based on the serial number of the cartridge. This information can then be used to be control or meter the dose of vapor inhaled by the user. The app can further track when the cartridge is running out of liquid or oil, and can further be configured to prompt the user to replace or order a new cartridge, as well as being able to order a new cartridge automatically.

In some embodiments, the vape device can be locked and unlocked by the user with their personal computing device. In some embodiments, the vape pen can be unlocked by the user by opening their personal computing device by satisfying the device's security settings, that is, by the user entering their security access code or password into the personal computing device, or by using a fingerprint scanner disposed on the personal computing device, or by using a camera disposed on the device for facial or retinal scans of the user. In some embodiments, the vape device can be configured to be child-resistant, as well as prevent use by an unauthorized user. In some embodiments, the vape device can be configured to lock inherently when not connected to the app for regulatory purposes. In some embodiments, the vape device can further comprise means for identifying an authorized user when connectivity with the user's smart phone or device is lost, such as when the user does not have their smart phone or device, or when the battery in the smart phone or device becomes depleted. Such means can include a fingerprint sensor disposed on the vape device itself, wherein the vape device can retain personal data on the user such as one or more fingerprint scan data stored in a memory on the vape device in order to determine whether a fingerprint scan taken by the fingerprint sensor matches the fingerprint scan data stored in the memory to confirm the identity of the person attempting to use the vape device is an authorized user.

Broadly stated, in some embodiments, an improved vape device can be provided, comprising: an atomizer comprising a heating coil, the atomizer further comprising an inlet and an outlet; a mouthpiece operatively coupled to the outlet; and a payload reservoir operatively coupled to the inlet, the payload reservoir comprising an identifier ("ID") tag comprising a unique identifier for the payload reservoir, the payload reservoir configured to hold liquid or oil that can be drawn into the atomizer to be vaporized when the user draws on the mouthpiece.

Broadly stated, in some embodiments, the vape device can further comprise a radio frequency transceiver or wireless transceiver and at least one antenna operatively coupled to the transceiver, the combination of the transceiver and the antenna configured for enabling the wireless transmission of data between the vape device and a personal computing device.

Broadly stated, in some embodiments, an improved vape device system can be provided, the system comprising a vape device comprising: an atomizer comprising a heating coil, the atomizer further comprising an inlet and an outlet, a mouthpiece operatively coupled to the outlet, a payload reservoir operatively coupled to the inlet, the payload reservoir comprising an identifier ("ID") tag comprising a unique identifier for the payload reservoir, the payload reservoir configured to hold liquid or oil that can be drawn into the atomizer to be vaporized when the user draws on the mouthpiece, and a radio frequency transceiver and at least one antenna operatively coupled to the transceiver, the combination of the transceiver and the at least one antenna configured for wirelessly transmitting and receiving data; and a personal computing device configured for the wireless transmission of the data to and from the vape device.

Broadly stated, in some embodiments, the vape device can further comprise a switch or a draw sensor operatively coupled to the mouthpiece, the switch or the draw sensor configured to cause electrical current to flow through the heating coil when the switch is operated or when the user draws on the mouthpiece.

Broadly stated, in some embodiments, the vape device can further comprise a battery configured to provide the electrical current.

Broadly stated, in some embodiments, the vape device can further comprise a battery charger configured for charging the battery.

Broadly stated, in some embodiments, the personal computing device can comprise a software application running thereon, wherein the combination of the vape device and the personal computing device can be configured for wireless control of the vape device using the personal computing device.

Broadly stated, in some embodiments, the software application can be further configured for carrying out the steps of: interpreting the ID tag via first data transmitted to the personal computing device from the vape device, the first data comprising the unique payload identifier; using the unique identifier to determine what liquid or oil is in the payload reservoir; and transmitting an operational setting to the vape device from the personal computing device, the operational setting comprising instructions to the vape device to either enable operation of the vape device if the user is authorized to use the vape device or to disable operation of the vape device if the user is not authorized to use the vape device.

Broadly stated, in some embodiments, the operational setting can further comprise instructions to the vape device to either enable operation of the vape device if the user is located in a geographic region where the liquid or oil can be vaporized by the user and to disable operation of the vape device if the user is located in a geographic region where the liquid or oil cannot be vaporized by the user.

Broadly stated, in some embodiments, the vape device can further comprise a microcontroller operatively coupled to the atomizer and to the ID tag, the microcontroller configured to control the operation of the vape device.

Broadly stated, in some embodiments, the vape device can further comprise a user interface operatively coupled to the microcontroller.

Broadly stated, in some embodiments, the user interface can comprise one or more user input control devices operatively coupled to the microcontroller, the input control devices configured for controlling the operation of the vape device when operated by the user.

Broadly stated, in some embodiments, the user interface can further comprise one or more user output indicating devices operatively coupled to the microcontroller, the output indicating devices configured for relaying information on the operation of the vape device to the user.

Broadly stated, in some embodiments, the atomizer can be disposed in an atomizer assembly; the mouthpiece and the payload reservoir can be both disposed in a mouthpiece assembly; and the microcontroller can be disposed in a control assembly, wherein the atomizer assembly can be disposed between the mouthpiece assembly and the control assembly.

In one preferred embodiment, a vape device system includes an atomizer having an inlet and an outlet, a mouthpiece coupled to the outlet, an activation mechanism coupled to the atomizer, a payload reservoir coupled to the inlet, and a processor. The payload reservoir is identified by a payload identifier, and the payload reservoir is configured to hold a substance for vaporization. The processor is configured to determine an operational setting based on at least one of the payload identifier and a secondary data.

The processor may be physically coupled directly or indirectly to at least one of the atomizer, the mouthpiece, the activation mechanism, and the payload reservoir. Alternatively, the system may include (i) a vape device comprising the atomizer, the mouthpiece, the activation mechanism, the payload reservoir, a second processor, and a wireless transceiver, and (ii) a computing device comprising the processor. The second processor is preferably configured to receive the payload identifier and transmit the payload identifier to the wireless transceiver. The wireless transceiver is preferably configured to transmit the payload identifier to the processor, and the wireless transceiver is preferably further configured to receive the operational setting from the processor and transmit the operational setting to the second processor.

The secondary data is preferably selected from a group consisting of user information, prescription information, location information, and payload information. The operational setting preferably includes at least one of a duty cycle setting, a temperature setting, an operational time duration, a dosage setting, and a security setting.

A method of controlling a vape device comprising a payload reservoir that is identified by a payload identifier includes steps of transmitting the payload identifier to a processor, determining an operational setting of the vape device with the processor based on the payload identifier and a secondary data, and controlling the vape device based on the operational setting.

The processor may be located in a computing device remotely from the vape device, wherein the vape device comprises a second processor that receives the payload identifier and transmits the payload identifier to a wireless transceiver of the vape device. The wireless transceiver preferably transmits the payload identifier to the processor, and the wireless transceiver preferably receives the operational setting from the processor and transmits the operational setting to the second processor.

The secondary data may be historical vape device usage information or historical payload reservoir information, and the operational setting includes at least one of a duty cycle setting, a temperature setting, an operational time duration, and a dosage setting. The secondary data may be prescription information, and the operational setting includes at least one of a duty cycle setting, a temperature setting, an operational time duration, and a dosage setting.

The secondary data may be location information, and the operational setting is a security setting of the vape device. The secondary data may be user information, and the operational setting is a security setting of the vape device. The secondary data may be user information, and the operational setting includes at least one of a duty cycle setting, a temperature setting, an operational time duration, and a dosage setting.

A method of determining an operational setting of a vape device comprising a payload reservoir that is identified by a payload identifier includes steps of authenticating a user via a software application on a computing device, transmitting the payload identifier from a wireless transceiver of the vape device to the computing device, determining the operational setting with the computing device based at least in part on the payload identifier or a secondary data, transmitting the operational setting from the computing device to the vape device, and controlling the vape device based on the operational setting. The secondary data and operational settings may be any of those described above. The method may comprise unlocking or locking the vape device based on a detected motion, acceleration, altitude, or velocity of the vape device or the computing device.

A system for authorizing operation of a vape device in accordance with another exemplary embodiment of the invention includes a vape device and an application configured to be installed on a personal computing device. The vape device is configured to store a unique payload identifier that identifies the payload reservoir and transmit the unique payload identifier to the personal computing device. The application is configured to enable the personal computing device to (a) confirm an identity of a user in possession of the computing device, (b) poll the vape device for the unique payload identifier if the identity of the user is confirmed, (c) receive the unique payload identifier from the vape device, (d) utilize the unique payload identifier to determine whether the user is authorized to use the payload reservoir, (e) generate a security setting indicating whether the user is authorized to use the payload reservoir, and (f) transmit the security setting to the vape device.

A system for authenticating users of vape devices in accordance with another exemplary embodiment of the invention includes a vape device and an application configured to be installed on a personal computing device. The vape device is configured to store a unique payload identifier that identifies the payload reservoir and transmit the unique payload identifier to the personal computing device. The application is configured to enable the personal computing device to (a) receive user authentication information input by a user, (b) receive the unique payload identifier from the vape device, (c) retrieve authentication information stored in association with the unique payload identifier in a database, (d) compare the user authentication information with the authentication information stored in the database, (e) generate, based on the comparison, a security setting indicating whether the user who input the user authentication information is authorized to use a payload reservoir identified by the unique payload identifier, and (f) transmit the security setting to the vape device.

A system for determining whether payload reservoirs of vape devices are depleted in accordance with another exemplary embodiment of the invention includes a vape device and an application configured to be installed on a personal computing device. The vape device is configured to store a unique payload identifier that identifies the payload reservoir and transmit the unique payload identifier to the personal computing device. The application is configured to enable the personal computing device to (a) receive the unique payload identifier from the vape device, (b) retrieve payload information stored in association with the unique payload identifier in a database, wherein the payload information comprises an original volume of the payload contained within the payload reservoir, (c) retrieve historical payload reservoir usage information stored in association with the unique payload identifier in the database, (d) analyze the payload information stored in the database and the historical payload reservoir usage information stored in the database, (e) generate, based on the analysis, a security setting indicating whether the payload reservoir is depleted, and (f) transmit the security setting to the vape device, wherein operation of the vape device is prevented if the security setting indicates that the payload reservoir is depleted.

A system for determining whether payload reservoirs of vape devices have been returned to a return center in accordance with another exemplary embodiment of the invention includes a vape device and an application configured to be installed on a personal computing device. The vape device is configured to store a unique payload identifier that identifies the payload reservoir and transmit the unique payload identifier to the personal computing device. The application is configured to enable the personal computing device to (a) receive the unique payload identifier from the vape device, (b) determine whether the payload reservoir identified by the unique payload identifier has been returned, (c) generate a security setting indicating whether the payload reservoir has been returned, and (d) transmit the security setting to the vape device, wherein operation of the vape device is prevented if the security setting indicates that the payload reservoir has been returned.

A system for determining whether payload reservoirs of vape devices have been recalled in accordance with another exemplary embodiment of the invention includes a vape device and an application configured to be installed on a personal computing device. The vape device is configured to store a unique payload identifier that identifies the payload reservoir and transmit the unique payload identifier to the personal computing device. The application is configured to enable the personal computing device to (a) receive the unique payload identifier from the vape device, (b) determine whether the payload reservoir identified by the unique payload identifier has been recalled, (c) generate a security setting indicating whether the payload reservoir has been recalled, and (d) transmit the security setting to the vape device, wherein operation of the vape device is prevented if the security setting indicates that the payload reservoir has been recalled.

A system for determining whether control assemblies are authorized for use with cartridges of vape devices in accordance with another exemplary embodiment of the invention includes a vape device and an application configured to be installed on a personal computing device. The vape device comprises a control assembly and a cartridge. The control assembly is configured to store a control assembly identifier, and the cartridge is configured to store a unique payload identifier that identifies the payload reservoir of the cartridge. The vape device is configured to transmit the control assembly identifier and the unique payload identifier to a personal computing device. The application is configured to enable the personal computing device to (a) receive the control assembly identifier and the unique payload identifier from the vape device, (b) identify a list of one or more control assembly identifiers for control assemblies that are authorized for use with the payload reservoir identified by the unique identifier, (c) compare the control assembly identifier with the list of control assembly identifiers, (d) generate, based on the comparison, a security setting indicating whether the control assembly identified by the control assembly identifier is authorized for use with the payload reservoir identified by the unique payload identifier, and (e) transmit the security setting to the vape device.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF EXEMPLARY EMBODIMENTS

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, acts, etc. described in one embodiment may also be included in other embodiments, but is not necessarily included. Thus, the present technology can include a variety of combinations and/or integrations of the embodiments described herein.

First Embodiment of Vape Device

Figure 1:
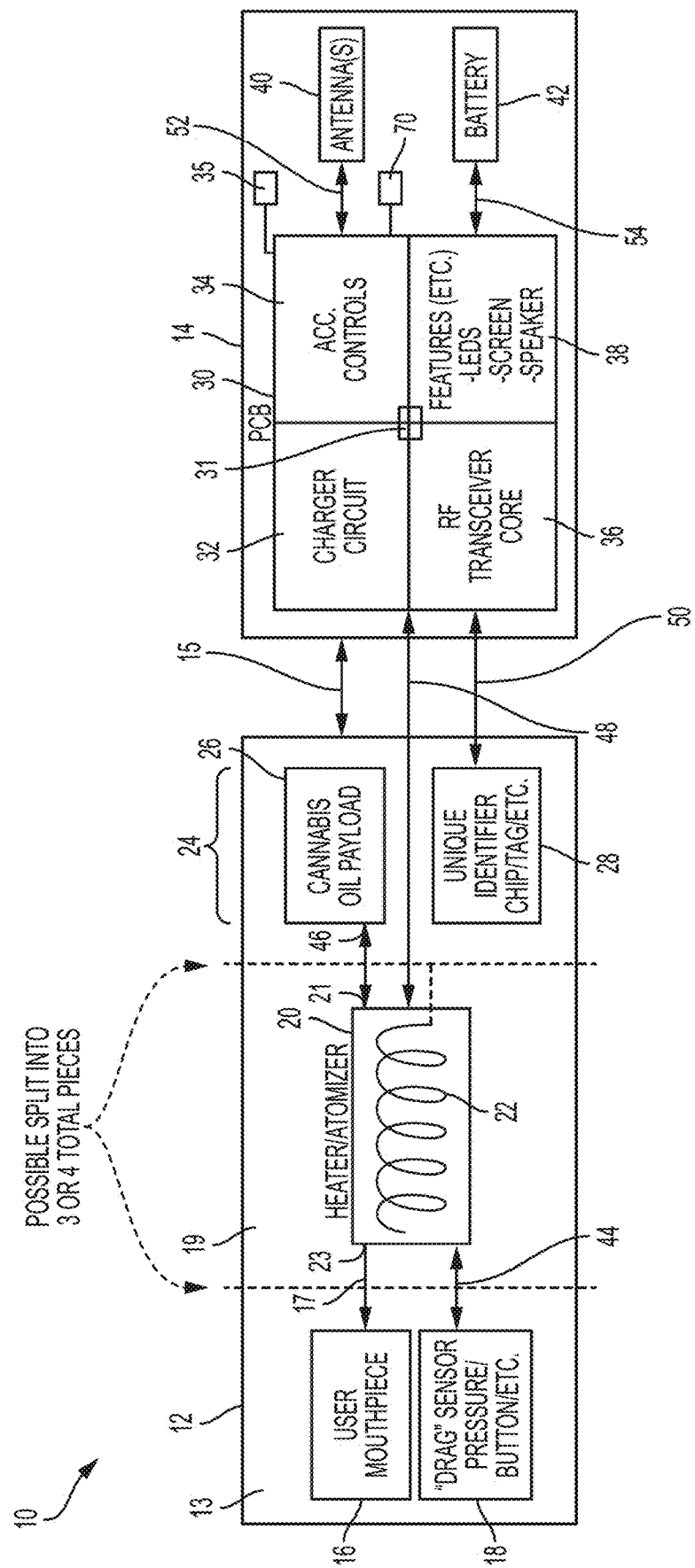
FIG. 1 is a block diagram depicting one embodiment of an improved vape device.

Referring to FIG. 1, one embodiment of vape device 10 is shown. Vape device 10 includes a mouthpiece assembly 12, an atomizer assembly 19, a payload assembly 24, and a control assembly 14. Any of mouthpiece assembly 12, atomizer assembly 19, payload assembly 24, and control assembly 14 may be formed integrally together and included within a common housing suitable for grasping by a user. Further, any of mouthpiece assembly 12, atomizer assembly 19, payload assembly 24, and control assembly 14 may be formed in separate housings that are releasably connected to each other via connecting means 15, which can comprise, for example, one or more of pressure or friction fit connection means, twist mechanical lock means, magnetic connection means and any other connecting means as well known to those skilled in the art. The connecting means 15 may include a female 510 threaded connector on the control assembly 14 that releasably engages a male 510 threaded connector on the atomizer assembly 19 or payload assembly 24. A 510 threaded connector, as is known in the art, is a M7-0.5×5 threaded connector, i.e., a threaded connector with a nominal diameter of 7 mm, a pitch of 0.5 mm, and a length of 5 mm. Connecting means 15 may include threaded connectors of other sizes. By way of example, mouthpiece assembly 12 may be releasably connected to atomizer assembly 19, payload assembly 24 and control assembly 14, which are either formed integrally together or in separate housings that are releasably connected to each other. Mouthpiece assembly 12 and atomizer assembly 19 may be formed integrally together and releasably connected to payload assembly 24 and control assembly 14, which are either formed integrally together or in separate housings that are releasably connected to each other. Further, mouthpiece assembly 12, atomizer assembly 19, and payload assembly 24 may be formed integrally together and releasably connected to control assembly 14. The combination of the mouthpiece assembly 12, atomizer assembly 19, and payload assembly 24 may be referred to as a cartridge herein. It is also within the scope of the invention for the mouthpiece assembly 12 to be omitted and for the vaporized payload to exit the atomizer assembly 19 directly for inhalation.

In some embodiments, mouthpiece assembly 12 is operatively coupled to control assembly 14 via connecting means 15. In some embodiments, a heater or atomizer 20 is disposed in atomizer assembly 19, with atomizer 20 further comprising a heating element 22 disposed therein for heating and vaporizing a payload that may comprise liquids, oils, other fluids, or tablets. Heating element 22 may be a heating coil. Atomizer 20 can comprise an inlet 21 and an outlet 23, wherein inlet 21 can be in communication, via fluid connector 46, with payload reservoir 26 disposed in payload assembly 24, wherein payload reservoir 26 can contain a payload for vaporization or atomization. The payload may be for example, liquids, oils, other fluids, or tablets. The payload may comprise cannabis oil or nicotine oil. Outlet 23 can be in communication with a user mouthpiece 16 of mouthpiece assembly 12 via a conduit 17. In some embodiments, payload assembly 24 can comprise an identifier ("ID") tag 28, which can further comprise a unique payload identifier that identifies payload reservoir 26, and also optionally, secondary data as described below. The unique payload identifier of ID tag 28 may be a serial number or tracking number for payload reservoir 26 as a means to identify what payload is contained in payload reservoir 26 so as to obtain information as to the specific parameters of operation of atomizer 20, or operational settings, that are optimal for vaporizing the specific payload contained in payload reservoir 26. For example, the payload identifier may be compared to a database that includes the payload identifiers from a plurality of payload reservoirs. The database may include specific operational settings and secondary data for each of the payload identifiers, as described below.

ID tag 28 may be any type of device that includes memory or storage capable of storing payload identifier and, optionally, secondary data, and means for allowing that payload identifier and/or secondary data to be retrieved by another device, such as microcontroller 31 and/or RF transceiver circuit 36, for processing and/or further transmission. For example, ID tag 28 may be an RFID tag or non-volatile memory. ID tag 28 may be configured for use with NFC or a UHF RFID communication system.

For the purposes of this specification, the term "electrical connection" shall include any form of electrical connection via a wired or wireless connection, such as electrical conductors or wires suitable for the transmission of alternating or direct current power, analog or digital electrical signals or radio frequency signals, as the case may be and as well-known to those skilled in the art.

In some embodiments, mouthpiece assembly 12 can comprise a draw sensor 18 operatively coupled to atomizer 20 via an electrical connection 44, wherein draw sensor 18 can cause electric current from battery 42 to flow through heating element 22. In some embodiments, draw sensor 18 comprises a sensor, such as a mass air flow sensor, that can produce an electrical signal in response to when a user inhales or draws on mouthpiece 16, wherein the electrical signal can cause electric current from battery 42 to flow through heating element 22. In some embodiments, draw sensor 18 can be used as a simple "switch" as a means to turn on atomizer 20 to vaporize payload drawn into atomizer 20 from payload reservoir 26 as the user draws on mouthpiece 16. In some embodiments, draw sensor 18 can be configured to monitor how much payload is being vaporized or how much volume of vapor is being inhaled by the user. Draw sensor 18 is one type of activation mechanism that may be used to activate atomizer 20. Draw sensor 18 may be replaced with or used in connection with another type of activation mechanism that receives an input to switch it from an off position, in which atomizer 20 is not activated, and a on position, in which atomizer 20 is activated. For example, draw sensor 18 may be replaced with or used in connection with any of the following types of activation mechanisms: a button, switch, draw sensor, pressure transducer, proximity sensor, touch sensor, voice recognition sensor, haptic control, saliva and breath biosensor, and the like.

In some embodiments, mouthpiece 16 and draw sensor 18 can be part of a single-piece mouthpiece assembly 12, or can be disposed in a separate mouthpiece section 13 that forms part of mouthpiece assembly 12.

In some embodiments, atomizer 20 can be disposed in atomizer assembly 19 that can either be integral to mouthpiece assembly 12, or a physically separate enclosure that can couple to mouthpiece assembly 12. Instead of or in addition to including a heating element 22 as disclosed herein, atomizer 20 may include any other structure capable of vaporizing or atomizing a payload in a suitable form for inhalation. For example, atomizer 20 may include a jet nebulizer, an ultrasonic nebulizer, or a mesh nebulizer.

In some embodiments, payload reservoir 26 and ID tag 28 can be disposed in payload assembly 24 that can either be integral to mouthpiece assembly 12 and/or atomizer assembly 19, or a physically separate enclosure that can couple to mouthpiece assembly 12 and/or atomizer assembly 19, which can include one or more of connecting means 15 described above. Preferably, ID tag 28 is physically coupled to payload reservoir 26 either directly or indirectly (e.g., ID tag 28 and payload reservoir 26 are included in a common housing of payload assembly 24) in a tamper resistant manner.

In some embodiments, control assembly 14 can comprise one or more antennas 40, a battery 42 and a circuit board 30 that can further comprise a microcontroller 31 configured for carrying out one or more electronic functions in respect of the operation of vape device 10. Having more than one antenna 40 can enable the ability for diversity wireless communications of RF signals, as well known to those skilled in the art. In some embodiments, circuit board 30 can comprise a charger circuit 32 configured for charging battery 42. Charger circuit 32 can be integral to circuit board 30 or can be disposed on a separate circuit board operatively connected to circuit board 30 and to battery 42 via electrical connection 54. Charger circuit 32 can be configured to be operatively connected to an external source of power, either via a shared or dedicated electrical connector 35 operatively coupled to circuit board 30 with internal connection to charger circuit 32, or a wireless connection for power transfer, as well known to those skilled in the art.

In some embodiments, circuit board 30 can comprise user input interface circuit 34 and output interface circuit 38. Either or both of input interface circuit 34 and output interface circuit 38 can be integral to circuit board 30 or can be disposed on a separate circuit board operatively connected to circuit board 30. In some embodiments, input interface circuit 34 can provide the electrical interface between user controls and activation mechanisms disposed on vape device 10, such as buttons, switches, draw sensors, pressure transducers, proximity sensors, touch sensors, voice recognition sensors, haptic controls, saliva and breath biosensors, and the like, and microcontroller 31 and, thus, can provide the means to relay user input commands from the user controls as instructions to microcontroller 31 to operate vape device 10. For example, input interface circuit 34 may be electrically coupled to draw sensor 18 for receiving an on signal from draw sensor 18 when a user draws on mouthpiece 16. When input interface circuit 34 receives the on signal from draw sensor 18, it may send instructions to microcontroller 31 to activate atomizer 20, provided that any other conditions necessary to activate atomizer 20 have been met, as described below. In some embodiments, output interface circuit 38 can provided the electrical interface between microcontroller 31 and output display devices, such as indicator lights, alphanumeric display screens, audio speakers, surface heaters, vibration devices, and any other forms of tactile feedback devices as well known to those skilled in the art, and, thus, can provide the means to relay information relating to the operation of vape device 10 from microcontroller 31 to the user.

Figure 3:
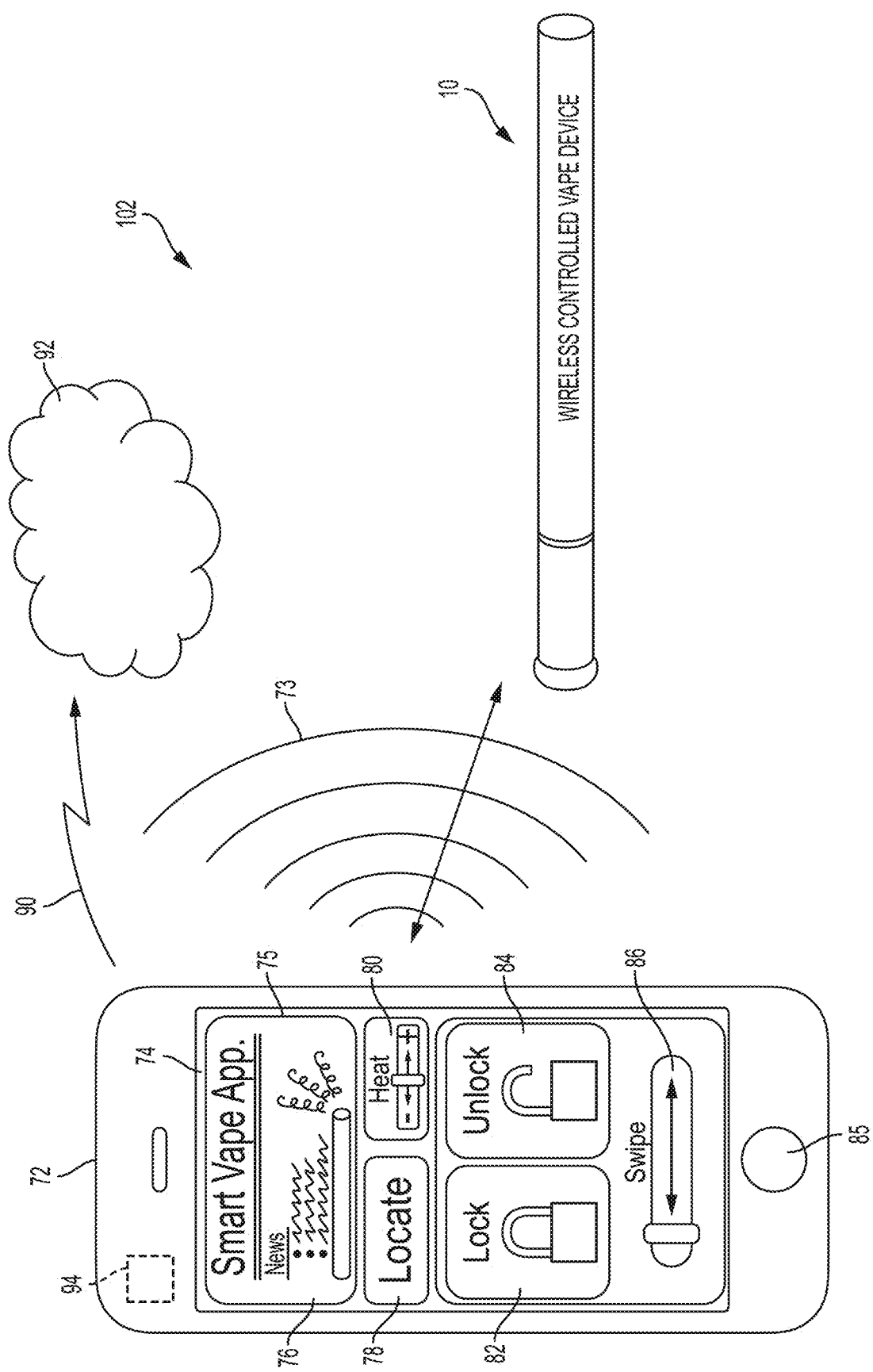
FIG. 3 is a block diagram depicting a vape device system comprising an improved vape device capable of wireless communication with a computing device.

In some embodiments, circuit board 30 can comprise radio frequency ("RF") transceiver circuit 36 to provide the means for wireless communication of data between vape device 10 and a personal computing device, such as computing device 72 as shown in FIG. 3. In some embodiments, RF transceiver circuit 36 can be integral to circuit board 30 or can be disposed on a separate circuit board operatively connected to circuit board 30. RF transceiver circuit 36 can be connected to one or more antennas 40 via electrical connection 52, as well known to those skilled in the art. RF transceiver circuit 36 and the one or more antennas 40 comprise a wireless transceiver of vape device 10.

In some embodiments, microcontroller 31 can comprise a microprocessor (which for purposes of this disclosure also incorporates any type of processor) having a central processing unit as well known to those skilled in the art, wherein the microprocessor can further comprise a memory configured for storing a series of instructions for operating the microprocessor in addition for storing data collected from sensors disposed on vape device 10 or data received by vape device 10 to control its operation, such as operational settings. Microcontroller 31 is in electrical communication with charger circuit 32, user input interface circuit 34, output interface circuit 38, and RF transceiver circuit 36 for receiving instructions and/or data from and/or transmitting instructions and/or data to charger circuit 32, user input interface circuit 34, output interface circuit 38, and RF transceiver circuit 36. In some embodiments, atomizer 20 can be operatively and electrically connected to circuit board 30 via electrical connection 48, which can provide the means to activate atomizer 20 (e.g., deliver electrical current from battery 42 to heating element 22) when an activation mechanism such as draw sensor 18 sends an on signal to microcontroller 31, as well as receiving data signals from draw sensor 18 and/or atomizer 20. In this manner, the activation mechanism (i.e., draw sensor 18) is coupled to the atomizer 20 indirectly through microcontroller 31, and a direct connection between the activation mechanism and atomizer 20 is not required (i.e., activation mechanism sends a signal to microcontroller 31 that sends a signal to activate atomizer 20). In addition to controlling operation of atomizer 20 based on a signal received from the activation mechanism, microcontroller 31 also controls operation of atomizer 20 based on the operational settings as described herein. In some embodiments, microcontroller 31 can be operatively connected to ID tag 28 via electrical connection 50, which may be either a wired or wireless connection.

The operational settings referred to herein include any type of setting or instruction that instructs the vape device 10 or certain components of the vape device 10 to operate or not operate in a particular manner. Specifically, operational settings of the vape device 10 include a duty cycle setting, a temperature setting, an operational time duration, a dosage setting, and a security setting. The duty cycle setting preferably corresponds to a pulse width modulation instruction transmitted from microcontroller 31 to battery 42 to send electrical current to heating element 22 in a particular desired manner. The temperature setting preferably corresponds to a temperature instruction transmitted from microcontroller 31 to battery 42 to send electrical current to heating element 22 to maintain heating element 22 at a desired temperature or range of temperatures. A temperature sensor may be coupled to microcontroller 31 to measure the actual temperature of heating element 22 and transmit that information to microcontroller 31 for determination on the amount and duration of electrical current that needs to be sent to heating element 22 to maintain a particular temperature or range of temperatures. The operational time duration preferably corresponds to a time instruction transmitted from microcontroller 31 to battery 42 to maintain heating element 22 at a temperature suitable for vaporization of the contents of payload reservoir 26 for a desired time. The dosage setting preferably corresponds to a dosage instruction transmitted from microcontroller 31 to battery 42 that powers down heating element 22 when a desired volume of vapor passes through atomizer 20. A vapor metering device may measure the volume of vapor passing through atomizer 20 and transmit that information to microcontroller 31, which compares the actual volume passed through atomizer 20 to the dosage setting to determine when to shut off heating element 22. The security setting preferably corresponds to a security instruction that causes microcontroller 31 to prevent operation of atomizer 20 when an event has or has not occurred. Security settings described herein that would prevent operation of atomizer 20 include a payload reservoir 26 that is tampered with or stolen, a payload reservoir 26 that has been returned to a return center (e.g., to recycle payload reservoir 26 and/or its associated cartridge), a payload reservoir 26 that has been recalled, a payload reservoir 26 that has been depleted, a control assembly that is not authorized for use with payload reservoir 26, an unauthorized user (e.g., a user who does not have a valid prescription for the substance within payload reservoir 26, or a user who is not identified as owning or having valid rights to use payload reservoir 26), a user that is in a location that does not permit use of vape device 10, a user that is traveling in a vehicle, a user that has exceeded his/her permitted usage of the substance in payload reservoir 26 within a particular time frame, and any other security setting described herein or reason why vape device 10 is rendered inoperable as described herein.

In some embodiments, ID tag 28 and/or microcontroller 31, along with appropriate sensors, can also be used as part of a system for gathering data relating to the use of vape device 10 by the user by monitoring that can include, without limitation, historical vape device usage information, such as how many times vape device 10 is used during a given period of time (hour, day, week, etc.), the duration of each use of vape device 10, how many draws the user takes on vape device 10, the strength of those draws, the amount of payload consumed during each use of vape device 10, and other information as described herein. The historical vape device usage information is stored in a database in association with the payload identifier, as described below. In some embodiments, the historical vape device usage information can be used as clinical data for determining whether the user is consuming the right amount of medicine to be vaporized and inhaled and at the right times of day. The information can be used to provide feedback to the user in terms of whether the user should consume medicine more frequently or less frequently throughout the day and/or to increase or decrease the amount of medicine consumed per usage overall or per usage at particular times of the day. In some embodiments, the information collected about the user's consumption of a cannabis liquid or oil payload with vape device 10 can be used to estimate the user's intoxication or impairment based on the user's physical characteristics and the amount of cannabis liquid or oil payload consumed. This estimation can be relayed to the user as a means to inform the user as to whether the user is too intoxicated or impaired to operate a motor vehicle or to operate tools or machinery, as an example.

Second Embodiment of Vape Device

Figure 2:
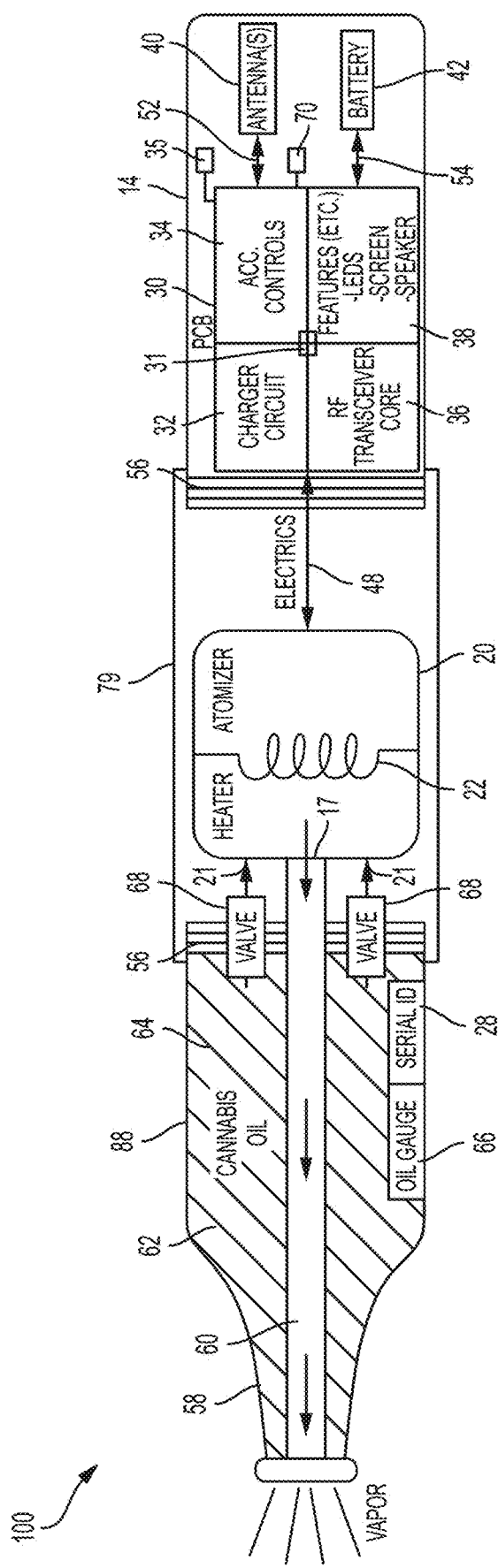
FIG. 2 is a block diagram depicting another embodiment of an improved vape device.

Referring to FIG. 2, another embodiment of vape device 100 is shown. In some embodiments, vape device 100 can comprise control assembly 14, atomizer assembly 79 and mouthpiece assembly 88 operatively coupled together in that order using mechanical connection means 56 to join the subassemblies together. Mechanical connection means 56 can comprise one or more of threaded connection means, magnetic connection means and friction or press-fit connection means, and any of the connection means 15 described above, including 510 threaded connectors. In some embodiments, mouthpiece assembly 88 can comprise a mouthpiece 58 in communication with the outlet of atomizer 20 via conduit 60. Mouthpiece assembly 88 can further comprise a payload reservoir 62 that can be filled with a payload 64 that may be liquid or oil. The payload 64 can flow from payload reservoir 62 to inlet 21 of atomizer 20 via one or more valves 68. In some embodiments, mouthpiece assembly 88 can comprise ID tag 28 and an oil gauge 66, which can be configured to monitor the volume of payload 64 in payload reservoir 62 and relay that information to microcontroller 31. In this embodiment, mouthpiece assembly 88 can be a consumable element that can be replaced as a complete assembly once depleted, or simply interchanged with another mouthpiece assembly 88 containing a different payload 64 for consumption, depending on the needs and wants of the user. In some embodiments, oil gauge 66 can simply be a sight glass disposed on mouthpiece assembly 88 to provide a visual indicator to the user as to the amount of payload remaining therein. Atomizer assembly 79 is preferably configured to prevent air-lock and/or clogging with thick, undiluted payloads.

In some embodiments, atomizer assembly 79 can also be a replaceable subcomponent of vape device 100 if and when atomizer 20 becomes damaged or simply ceases to work any further. In some embodiments, control assembly 14 can comprise sensors 70 electrically coupled to input interface circuit 34 along with user input buttons and controls (not shown) disposed on vape device 10 in addition to draw sensor 18, as described above and shown in FIG. 1.

Control assembly 14 of vape device 100 is preferably substantially similar to control assembly 14 of vape device 10. Atomizer 20 of vape device 100 is preferably substantially similar to atomizer 20 of vape device 10, and may include alternative means for vaporizing a payload other than a heating element as described above in connection with vape device 10. It is within the scope of the invention for atomizer assembly 79 and mouthpiece assembly 88 to be formed integrally within a common housing that is releasably connected to control assembly 14. Further, it is within the scope of the invention for control assembly 14 and atomizer assembly 79 to be formed integrally within a common housing that is releasably connected to mouthpiece assembly 88. It is also within the scope of the invention for atomizer assembly 79, mouthpiece assembly 88, and control assembly 14 to be formed integrally within a common housing.

Vape Device Application

Referring to FIG. 3, a vape device system 102 includes vape device 10 and computing device 72 running application 74 thereon. It is understood that computing device 72 includes a processor 94 that runs application 74, and that references herein to computing device 72 include its processor 94. Vape device 100 may also be operated with computing device 72 in the same manner as described below with respect to vape device 10. In some embodiments, vape device 10 can wirelessly communicate with computing device 72 and application 74 via RF communications link 73. In some embodiments, RF communications link 73 can comprise one or more of Bluetooth™ communications protocol, Wi-Fi™ IEEE 802 communications protocol, Zigbee IEEE 802.15.4-based protocol, and any other RF, short-range, and long-range communications protocol as well known to those skilled in the art. Vape device 10 may also communicate with computing device 72 via a wired connection established for example between electrical connector 35 of vape device 10 and a communications connector (not shown) of computing device 72.

In some embodiments, application 74 can present a visual "dashboard" 75 comprising of visual information and controls that can be operated by a user. In some embodiments, dashboard 75 can comprise user information window 76 for displaying information regarding the operation of vape device 10 in addition to general information. This general information can include general news as well as information on available updates for vape device 10 or the application 74 from the manufacturer or supplier of the same.

In some embodiments, dashboard 75 can comprise a locate button 78 as a means for the user to determine the location of vape device 10 should the user misplace it. By pressing locate button 78, computing device 72 can send a signal wirelessly to vape device 10 to operate an audible signal from an audio speaker or buzzer or other like device disposed thereon to assist the user in finding vape device 10. In other embodiments, pressing locate button 78 can assist the user to determine his or her geographic location (using geographic location capabilities of computing device 72) and whether cannabis products can be consumed using vape device 10 in that location (e.g., whether there are any governmental regulations, laws, or rules applicable to or enforceable in the geographic area where vape device 10 is located that may subject the user of vape device 10 to criminal or administrative penalties, fines, or enforcement actions). In some embodiments, dashboard 75 can comprise heat swipe button 80 as a means for the user to manually control the heat used to vaporize payload 64, wherein the signal transmitted by application 74 to vape device 10 to control the heat can be included in the operational setting. In some embodiments, dashboard 75 can comprise lock indicator 82, unlock indicator 84 and swipe button 86 as a means to enable and disable vape device 10 by the user swiping swipe button 86 right or left, respectively.

In some embodiments, the application 74 can access an online source of data to update the database (described below) or otherwise process information, which can be done periodically and/or automatically, or manually by the user prompting the application to update the data, or a combination of both processes. As described below, the online source of data may include operational settings for a plurality of vape devices 10 and substances contained with payload reservoirs 26. The online source of data may also include a list of payload identifiers that have been stolen, a list of payload identifiers that have been recalled, and/or a list of payload identifiers that have been returned to a return center (e.g., for recycling). In addition, the online source of data may include a list of control assemblies that are authorized for use with each payload reservoir 26. In one embodiment, each control assembly is identified by a control assembly identifier, and the online source of data comprises a list of control assembly identifiers for control assemblies that are authorized for use with each payload reservoir 26.

Database

In some embodiments, a database is provided that stores the unique payload identifiers for a plurality of payload reservoirs and associates each of the unique payload identifiers with specific operational settings and/or secondary data. The secondary data may comprise, for example, user information, authentication information, prescription information, payload information, historical usage information (including historical vape device usage information and historical payload reservoir information), recall information, return information, and control assembly information, as described below. Of course, it should be understood that the database may store any combination of operational settings and secondary data as required for a particular application.

User information can include, but is not limited to, various physiological characteristics, such as a user's height, weight, age, gender, medical record and histories, and medical conditions.

User information can also include demographic information, such as a user's employer, employment history, educational history, criminal history, and the like. Not only can such user information be used for controlling operational settings of the vape device 10, but demographic information can be used to display targeted content, advertisements, and material on the dashboard 75 and/or user information window 76.

User information can be retrieved from, for example, third-party health, fitness, and social networking software applications on the computing device 72, such as Facebook®, LinkedIn®, Snapchat®, Twitter®, and/or Fitbit®. In addition, user information can be retrieved by application 74 or a remote computing device from third-party databases, such as health information databases, medical records databases, health insurance company databases, crime databases, legal and court databases, and the like. Further, user information can be entered into the application 74 and/or vape device 10 (via, e.g., user input devices coupled to user input interface circuit 34) by the user.

Authentication information can include a password or passcode, a fingerprint scan, a facial recognition scan, a retinal scan, or any other type of biometric information that can be used to identify a user. Authentication information can be entered into personal computing device 72 and/or vape device 10 (via, e.g., user input devices coupled to user input interface circuit 34) by the user.

Prescription information can be retrieved from, for example, pharmacy and dispensary databases, as well as from physicians, pharmacists, and others licensed to write and/or manage prescriptions. The prescription information preferably includes whether a particular user has a valid, unexpired prescription to use the substance within payload reservoir 26.

Payload information may include an identification of the particular substance located within a payload reservoir 26 and the original volume of the substance located within payload reservoir 26.

Historical usage information may include information associated with use of the vape device 10 (historical vape device usage information) and/or information associated with use of the payload reservoir 26 (historical payload reservoir information). The historical vape device usage information can include, but is not limited to, the number of prior sessions during which the vape device 10 was used, user information related to prior sessions, durations of prior sessions, operational settings of prior sessions, metering and dose information of prior sessions, and the like. The historical payload reservoir information can include details related to the payload reservoir 26, such as the original payload contents, remaining contents, used contents, content usage by session, and the like.

Recall information may include information indicating that payload reservoir 26 has been recalled. Return information may include information indicating that payload reservoir 26 has been returned to a return center (e.g., for recycling). Control assembly information may include information on control assemblies that are authorized for use with payload reservoir 26. In one embodiment, each control assembly is identified by a control assembly identifier, and the control assembly information comprises a list of control assembly identifiers for control assemblies that are authorized for use with payload reservoir 26.

It should be understood that the database may be maintained in memory of computing device 72 that is accessible by application 74, in memory of microcontroller 31, and/or in an external memory remote from vape device 10 and computing device 72 that is accessible via a global telecommunications network 92. Any type of relational database software may be used to maintain the data in the applicable memory, such as the Microsoft Access® software sold by Microsoft Corporation, the Oracle® software sold by Oracle Corporation, or the SQL software sold by Sybase, Inc. Of course, other database software may also be used as is known to those skilled in the art.

Method of Using Vape Device

Figure 4:
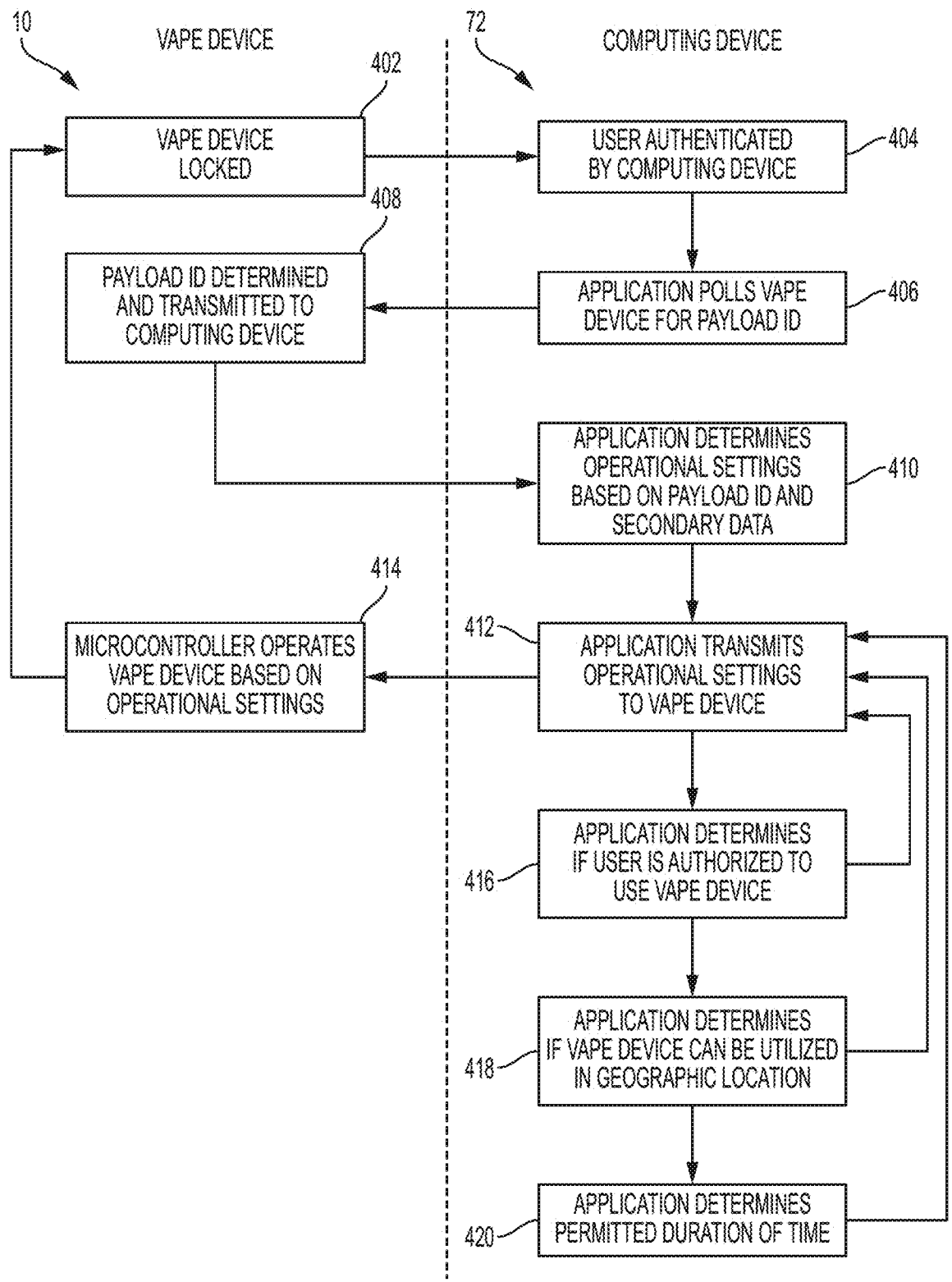
FIG. 4 is a flowchart depicting one embodiment of the steps carried out by the system of FIG. 3.

Referring to FIG. 4, steps in accordance with one exemplary method for operating and controlling vape device 10 and 100 are shown. Although the method is described below in connection with vape device 10, the method may also be used with vape device 100. The method may be carried out by vape device 10 in connection with application 74 running on computing device 72, shown in FIG. 3. The method may start at step 402 with vape device 10 in a default, locked state, meaning, it cannot be operated. When a user gains access to their computing device 72 at step 404, the computing device 72 can confirm the user's identification (e.g., by the user entering a password, passcode, or biometric authentication) so as to be able to move to step 406, where the computing device 72 can open the application 74 and then communicate with vape device 10 to poll for the unique payload identifier of ID tag 28. The application 74 may also be used to authenticate the user prior to transmission of the payload identifier to the computing device 72. At step 408, vape device 10 can, upon being polled by the computing device 72, read ID tag 28 and then transmit the payload identifier to the computing device 72. Specifically, in one embodiment, microcontroller 31 of vape device 10 receives the payload identifier from ID tag 28, transmits the payload identifier to the wireless transceiver (i.e., RF transceiver circuit 36 and antenna(s) 40), and the antenna(s) 40 transmit the payload identifier to computing device 72.

In step 410, the application 74 can utilize the payload identifier of ID tag 28, and optionally, secondary data, to determine the vaporizing or operational settings associated with the payload identifier of ID tag 28, and optionally, as well as in light of the secondary data. As described above, computing device 72 can alternatively transmit the unique payload identifier to a remote computing device at a central server or in the cloud. The remote computing device may maintain a database of operational settings that are associated with each unique payload identifier and tailored to the particular substance located in the payload reservoir 26 and the particular user using the payload reservoir 26. The remote computing device may then send the operational settings and identification of the specific substance within the payload reservoir 26 back to the computing device 72. In some embodiments, the application 74 proceeds to step 412 and transmits the operational settings to vape device 10. Specifically, in one embodiment, a wireless transceiver of computing device 72 transmits the operational settings to the antenna(s) 40 and RF transceiver circuit 36 of vape device, which transmits the operational settings to the microprocessor of microcontroller 31. In step 414, the microcontroller 31 in the vape device 10 then operates and controls the vape device 10 based on the operational settings.

In other embodiments, the application 74 proceeds to step 416 instead of step 414, whereupon the application 74 can confirm whether the user is authorized to use vape device 10. Application 74 can utilize any combination of secondary data (e.g., user information, prescription information, location information, payload information, historical vape device usage information, and historical payload reservoir information) and the payload identifier in order to determine if the user is authorized to use the vape device 10. For example, application 74 can use secondary data such as prescription information, as well as payload information indicating the contents of the payload reservoir 26, to determine if the prescription associated with the prescription information allows the user to access the payload contents within payload reservoir 26.

In yet another example, application 74 can utilize user information such as gender, age, and weight, as well as historical vape device usage information, to determine an appropriate dosage and/or metering of the vape device 10.

If the user is so authorized, the application 74 can further determine whether payload reservoir 26 (in FIG. 1) or mouthpiece assembly 88 (in FIG. 2) is genuine and not a counterfeit or, optionally, whether it is stolen or otherwise not authorized for use by the user (e.g., the application 74 may compare the payload identifier to payload information that indicates whether the payload reservoir 26 or mouthpiece assembly 88 has been reported as tampered with or stolen). If genuine and not stolen, then the application 74 can proceed to step 412 where the operational settings can be transmitted to vape device 10 and the user is subsequently allowed to operate vape device 10 in step 414. If not genuine or stolen, the application 74 can lock vape device 10 to prevent its use.

In other embodiments, the application 74 proceeds from step 416 to step 418, instead of proceeding to step 414. In step 418, the application 74 can determine the geographic location of vape device 10 and whether the payload in vape device 10 can be consumed in that location by comparing the geographic location to location information obtained by the application 74. If the payload in vape device 10 can be consumed in the location of vape device 10, the application 74 can proceed to step 412 where the operational settings can be transmitted to vape device 10, and the user is subsequently allowed to operate vape device 10 in step 414. If the payload in vape device 10 cannot be consumed in the location of vape device 10, the application 74 can lock vape device 10 to prevent its use.

In other embodiments, the application 74 proceeds to step 420 where a permitted duration of time that the vape device 10 can be used is determined. The permitted duration of time can be determined based on any combination of secondary data (e.g., user information, prescription information, location information, payload information, historical vape device usage information, and historical payload reservoir information) and/or the payload identifier. The permitted duration of time can be transmitted to the vape device as an operational setting in step 412. Once the operational settings are received by vape device 10 at step 414, vape device 10 can implement these operational settings to vaporize the payload contained therein accordingly. In this embodiment, vape device 10 can unlock for use by the user in accordance with the received operational settings. In addition, the vape device 10 can be locked in step 402 after the permitted duration of time or usage has expired.

In addition, after the vape device 10 is operated in step 414, vape device 10, either via the microcontroller 31 and/or the application 74, can be locked in step 402 after use, after a predetermined duration, after being deactivated by the user, after the payload reservoir 26 is deemed or calculated to be empty or used, after a new user has been detected, and/or for any other reason that vape device 10 may be locked as described herein.

In one embodiment, the method shown in FIG. 4 may be carried out by vape device 10 running application 74, or an application similar thereto, on the microprocessor of microcontroller 31 without use of computing device 72. In such an embodiment, step 402 remains the same as described above. Step 404 may be modified so that user information is inputted into vape device 10 to determine whether the user is an approved user of vape device 10 and the contents of payload reservoir 26. Steps 406 and 408 may be omitted, or optionally, step 408 may comprise the microprocessor of microcontroller 31 receiving the payload identifier from ID tag 28. In step 410, operational settings are determined based on the payload identifier and/or the secondary data as described above but they are determined by the microprocessor of microcontroller 31 of vape device 10. Step 412 is omitted as the operational settings are already contained on vape device 10. Step 414 proceeds as described above. Optional steps 416, 418, and 420 may proceed as described above but with an application running on the microprocessor of microcontroller 31 carrying out the steps.

In yet another embodiment, the computing device 72 is integrated within, or physically coupled to, the vape device 10. In this embodiment, the payload identifier can be transmitted to the computing device 72 via an electrical connection between the payload reservoir 26 and the integral computing device 72. Similarly, the computing device 72 can transmit the operational settings via the electrical connection to the microcontroller 31. In yet another embodiment, the integral computing device 72 can include a wireless transceiver, or an optical transceiver, and can operate as in the remote computing device embodiments described herein.

In some embodiments, vape devices 10 and 100 can comprise security settings to prevent unauthorized use of the vape devices by anyone other than the owner of the vape devices who has a prescription for medical marijuana. In some embodiments, the security settings can prevent the use of the vape devices in regions or jurisdictions, even by the rightful owner of the vape devices, where the consumption of medical marijuana is not authorized or legal. These security settings can be implemented to appease government or law enforcement for unauthorized use of the vape devices in the consumption of cannabis products, for medical purposes or otherwise.

In another embodiment, application 74 and/or vape device 10 can utilize acceleration, motion, altitude, and/or velocity sensors to determine if the user is within, for example, a moving vehicle or airplane. Such information can be used by application 74 and/or vape device 10 to restrict access to, or lock, the vape device 10. Sensors 70 such as accelerometers, altimeters, gyroscopes, and velocity sensors may be integrated with the vape device 10 and/or the computing device 72.

Of course, it should be understood that the invention is not limited to the exemplary method for operating and controlling a vape device as described above in connection with FIG. 4, and that other steps and combinations of steps for operating and controlling a vape device using a computing device running application 74 may be used.

In some embodiments, computing device 72 runs an application 74 comprising a set of instructions stored in the memory of computing device 72 and executable by the processor of computing device 72 to perform the processes described herein. Application 74 causes computing device 72 to retrieve the unique payload identifier, wherein the unique payload identifier and any combination of operational settings and secondary data stored in the database in association with the unique payload identifier, as described above, are used to modify, determine, adjust, or otherwise control the operational settings of, and access to, the vape device. In these embodiments, the database may be maintained in memory of computing device 72 that is accessible by application 74 and/or in an external memory remote from the vape device and computing device 72 that is accessible via a global telecommunications network 92.

In other embodiments, computing device 72 can retrieve the unique payload identifier from the vape device and transmit the unique payload identifier to a remote computing device via global telecommunications network 92, such as a computing device located at a central server or in the cloud. The remote computing device runs an application comprising a set of instructions stored in the memory of the remote computing device and executable by the processor of the remote computing device to perform the processes described herein. The remote computing device utilizes the unique payload identifier and any combination of operational settings and secondary data stored in the database in association with the unique payload identifier, as described above, in order to determine the operational and/or security settings for the vape device and transmit the operational and/or security settings back to computing device 72.

In some embodiments, the application (whether application 74 running on computing device 72 or an application running on the remote computing device) can use the unique payload identifier as a means to determine the operational settings of the vape device. In one embodiment, upon receipt of the unique payload identifier, the application can retrieve operational settings stored in association with the unique payload identifier in the database. The operational settings comprise operational settings for the vape device to vaporize the specific payload contained in the payload reservoir identified by the unique payload identifier as per the recommended settings from the manufacturer of the payload and/or vape device. In another embodiment, upon receipt of the unique payload identifier, the application can retrieve payload information stored in association with the unique payload identifier in the database. The payload information can include an identification of the substance contained in the payload reservoir identified by the unique payload identifier, and the application can access the operational settings associated with that substance via a connection to an online source of data. In another embodiment, the application can access the online source of data to update the operational settings stored in the database, which can be done periodically and automatically, or manually by the user prompting the application to update the data, or a combination of both processes. The operational settings (whether stored in the database or accessed via a connection to an online source of data) may be updated by the manufacturer or provider of the payload reservoir or vape device when new information is learned about the specific substance.

Once the operational settings have been determined as described above, the application causes transmission of the operational settings to the vape device whereby the vape device operates in accordance with the operational settings. Preferably, the vape device checks for new operational settings each time a user uses the vape device so that if the operational settings have been updated, the vape device operates in accordance with the updated operational settings. In this manner, a manufacturer or provider of the payload reservoir or vape device may update operational settings for a specific substance and specific payload reservoirs and be ensured that they will take effect for any future usage of the particular substance and payload reservoirs affected.

In some embodiments, application 74 running on computing device 72 can use the unique payload identifier as a means to determine if the person in possession of the vape device and computing device 72 is an authorized user.

In one embodiment, application 74 can request the user to input user authentication information, such as a password, a fingerprint scan, a facial recognition scan, a retinal scan, or other biometric information. Upon receipt of the unique payload identifier, application 74 can retrieve authentication information stored in association with the unique payload identifier in the database. Application 74 can then compare the user authentication information input by the user with the authentication information stored in the database and generate, based on the comparison, a security setting indicating whether the user who input the user authentication information is authorized to use the payload reservoir identified by the unique payload identifier. Application 74 can then cause transmission of the security setting (e.g., an enable or disable control signal) to the vape device. Operation of the vape device is prevented if the security setting indicates that the user who input the user authentication information is not authorized to use the payload reservoir identified by the unique payload identifier. However, operation of the vape device is allowed if the security setting indicates that the user who input the user authentication information is authorized to use the payload reservoir identified by the unique payload identifier.

In another embodiment, the vape device can be unlocked when the user opens his/her personal computing device 72 and satisfies the device's general security settings, that is, by the user entering his/her security access code or password into the personal computing device, or by using a fingerprint scanner disposed on the personal computing device, or by using a camera disposed on the device for facial or retinal scans of the user, as well known to those skilled in the art. If the person in possession of computing device 72 and the vape device is permitted to open up applications on computing device 72 and, thus, access application 74, the identity of the user is confirmed and application 74 can send an enable signal to the vape device to poll for the unique payload identifier and allow the vape device to operate, provided that all other factors or conditions to allow operation of the vape device have been met. For example, application 74 can use the unique payload identifier to determine whether the user is authorized to use the payload reservoir, generate a security setting indicating whether the user is authorized to use the payload reservoir, and transmit the security setting to the vape device.

When computing device 72 "goes to sleep," is turned off or powers down due to a low battery charge condition, as well known to those skilled in the art, application 74 can send a disable signal to the vape device, to prevent the vape device from operating. Also, when the vape device and computing device 72 are separated by a predetermined physical distance, the vape device can turn off or become disabled until it receives an enable signal from computing device 72. In some embodiments, application 74 can require the input of user authentication information associated with a security feature of the application (e.g., a password, a fingerprint scan, a facial recognition scan, or a retinal scan), in addition to any user authentication information to be entered or other security measure required by computing device 72 to unlock the vape device and enable opening up and enabling operation of application 74. If the user can enter the correct authentication information into application 74, then application 74 can send an enable signal to the vape device to poll for the unique payload identifier. Otherwise, while application 74 is closed, application 74 can send a disable signal to the vape device to disable it.

In some embodiments, once the identity of the user has been confirmed and application 74 has polled the vape device for the unique payload identifier, application 74 retrieves secondary data (e.g., user information, prescription information, payload information, historical vape device usage information, and/or historical payload reservoir information) stored in association with the unique payload identifier in the database, and optionally location information, and utilizes the secondary data and/or location information to determine whether the user is authorized to use the payload reservoir.

In some embodiments, if the user is authorized to use the payload reservoir, application 74 also utilizes the unique payload identifier to determine an operational setting for the vape device (e.g., a duty cycle setting, a temperature setting, an operational time duration, and a dosage setting). In one embodiment, application 74 retrieves an operational setting stored in association with the unique payload identifier in the database. In another embodiment, application 74 retrieves payload information stored in association with the unique payload identifier in the database, wherein the payload information comprises an identification of a substance located within the payload reservoir of the vape device. Application 74 then determines an operational setting associated with the substance, such as by retrieving the operational setting stored in association with the substance in another database. Other types of secondary data stored in association with the unique payload identifier may also be used to determine the operational setting. The operational setting may be transmitted to the vape device along with the security setting described above.

In yet another embodiment, application 74 can compare user information associated with the unique payload identifier (e.g., one or more particular users that can or cannot use the substance within the payload reservoir) with application user information that a user provides to application 74 to determine whether the user of application 74 is permitted to operate the vape device and use the particular payload reservoir.

In some embodiments, the application (whether application 74 running on computing device 72 or an application running on the remote computing device) can use the unique payload identifier as a means to determine if the payload can be consumed in the geographic region, location, country, state, or municipality where the user is located. In these embodiments, the application can access the global positioning system ("GPS") features that computing device 72 can possess to determine the physical location of computing device 72 and, thus, of its user. In other embodiments, computing device 72 can use cell tower triangulation techniques or other cell phone location techniques, as well known to those skilled in the art, to determine its geographical location.

Upon receipt of the unique payload identifier, the application can retrieve payload information stored in association with the unique payload identifier in the database. The application can then determine if the substance identified in the payload information can be legally consumed in the location of the user (i.e., the location of computing device 72). In one embodiment, this determination is made by comparing the geographic location of computing device 72 with a database of location information (that may be stored on computing device 72 or a remote computing device) to determine whether the user may legally consume the substance in that location. The application can then generate, based on the comparison, a security setting indicating whether the substance identified by the unique payload identifier can be legally consumed in the location of computing device 72. The application can then cause transmission of the security setting (e.g., an enable or disable control signal) to the vape device. Operation of the vape device is prevented if the security setting indicates that the substance identified by the unique payload identifier cannot be legally consumed in the location of computing device 72 (because its usage would violate laws or regulations or for any other reason). However, operation of the vape device is allowed if the security setting indicates that the substance identified by the unique payload identifier can be legally consumed in the location of computing device 72.

In some embodiments, the application (whether application 74 running on computing device 72 or an application running on the remote computing device) can use the unique payload identifier as a means to determine if a payload reservoir has been recalled, e.g., if a recall has been issued for the substance contained in the payload reservoir. In one embodiment, the application makes this determination by retrieving recall information stored in association with the unique payload identifier in the database, wherein the recall information indicates whether the payload reservoir has been recalled. In another embodiment, the application makes this determination by accessing an online source of data that identifies the payload reservoirs that have been recalled (or alternatively, the substances that have been recalled, which can be compared to the payload information stored in association with the unique payload identifier in the database). The application can then generate a security setting indicating whether the payload reservoir has been recalled and cause transmission of the security setting (e.g., an enable or disable control signal) to the vape device. Operation of the vape device is prevented if the security setting indicates that the payload reservoir has been recalled. However, operation of the vape device is allowed if the security setting indicates that the payload reservoir has not been recalled. This security feature also enables the display of a recall message and/or the sounding of an audible recall message on computing device 72 and/or the vape device itself. Of course, these recall messages would not be required if the payload reservoir was depleted, as described below.

In some embodiments, the application (whether application 74 running on computing device 72 or an application running on the remote computing device) can use the unique payload identifier as a means to determine if a payload reservoir has been returned to a return center, e.g., for recycling of a cartridge or payload reservoir. In one embodiment, the application makes this determination by retrieving return information stored in association with the unique payload identifier in the database, wherein the return information indicates whether the payload reservoir has been returned. In another embodiment, the application makes this determination by accessing an online source of data that identifies the payload reservoirs that have been returned. The application can then generate a security setting indicating whether the payload reservoir has been returned and cause transmission of the security setting (e.g., an enable or disable control signal) to the vape device. Operation of the vape device is prevented if the security setting indicates that the payload reservoir has been returned. However, operation of the vape device is allowed if the security setting indicates that the payload reservoir has not been returned.

In some embodiments, the application (whether application 74 running on computing device 72 or an application running on the remote computing device) can use the unique payload identifier as a means to determine if a payload reservoir has been stolen. In one embodiment, the application makes this determination by retrieving information stored in association with the unique payload identifier in the database, wherein the information indicates whether the payload reservoir has been stolen. In another embodiment, the application makes this determination by accessing an online source of data that identifies the payload reservoirs that have been stolen. The application can then generate a security setting indicating whether the payload reservoir has been stolen and cause transmission of the security setting (e.g., an enable or disable control signal) to the vape device.

Operation of the vape device is prevented if the security setting indicates that the payload reservoir has been stolen. However, operation of the vape device is allowed if the security setting indicates that the payload reservoir has not been stolen.

In some embodiments, the application (whether application 74 running on computing device 72 or an application running on the remote computing device) can use the unique payload identifier as a means to determine if a control assembly of the vape device is authorized for use with the payload reservoir contained in a cartridge of the vape device. In one embodiment, the application makes this determination by receiving a control assembly identifier for the control assembly of the vape device (which may be stored in the microcontroller of the control assembly and transmitted to the computing device 72 along with the unique payload identifier). In one embodiment, the control assembly identifier comprises a unique control assembly identifier, but this is optional and not required. The application then identifies a list of one or more control assembly identifiers for control assemblies that are authorized for use with the payload reservoir identified by the unique identifier. The application then compares the received control assembly identifier with the list of control assembly identifiers and, based on this comparison, generates a security setting indicating whether the control assembly identified by the received control assembly identifier is authorized for use with the payload reservoir identified by the received unique payload identifier. The application can then cause transmission of the security setting (e.g., an enable or disable control signal) to the vape device. Operation of the vape device is prevented if the security setting indicates that the control assembly identified by the control assembly identifier is not authorized for use with the payload reservoir identified by the unique payload identifier. However, operation of the vape device is allowed if the security setting indicates that if the security setting indicates that the control assembly identified by the control assembly identifier is authorized for use with the payload reservoir identified by the unique payload identifier.

In some embodiments, the application (whether application 74 running on computing device 72 or an application running on the remote computing device) can use the unique payload identifier as a means to determine whether the user of the vape device has a prescription for vaporizing the payload contained in the payload reservoir. In one embodiment, the application makes this determination by retrieving and analyzing user information and/or prescription information stored in association with the unique payload identifier in the database. The application can then generate a security setting indicating whether the user has a valid prescription for vaporizing the payload contained in the payload reservoir and cause transmission of the security setting (e.g., an enable or disable control signal) to the vape device. Operation of the vape device is prevented if the security setting indicates that the user does not have a valid prescription for vaporizing the payload contained in the payload reservoir. However, operation of the vape device is allowed if the security setting indicates that the user has a valid prescription for vaporizing the payload contained in the payload reservoir. Preferably, the prescription information is updated in the database when a user's prescription has changed.

In some embodiments, the application (whether application 74 running on computing device 72 or an application running on the remote computing device) can use the unique payload identifier as a means to determine whether the payload reservoir is depleted. In one embodiment, the application makes this determination by retrieving and analyzing payload information and historical payload reservoir usage information stored in association with the unique payload identifier in the database. The payload information includes the original volume of payload contained within the payload reservoir. The historical payload reservoir usage information is updated based on payload reservoir usage information obtained from the vape device, as described above. The application analyzes the payload information and the historical payload reservoir usage information to determine if the payload reservoir is depleted, e.g., if the current calculated volume of payload is below a predetermined threshold. The application then generates a security setting indicating whether the payload reservoir is depleted and causes transmission of the security setting (e.g., an enable or disable control signal) to the vape device. Operation of the vape device is prevented if the security setting indicates that the payload reservoir is depleted. However, operation of the vape device is allowed if the security setting indicates that the payload reservoir is not depleted. This security feature prevents the operation of vape devices with counterfeit payload reservoirs (e.g., a payload reservoir with the same unique identifier as a valid payload reservoir) or vape devices in which the payload reservoirs have been refilled without authorization. This security feature also prevents a user from dry vaping (i.e., inhaling without any payload in the payload reservoir), which provides improved consumer health.

In some embodiments, the application (whether application 74 running on computing device 72 or an application running on the remote computing device) can use the unique payload identifier as a means to determine when the payload reservoir is nearly empty of payload. In one embodiment, the application makes this determination by retrieving and analyzing payload information and historical payload reservoir usage information stored in association with the unique payload identifier in the database. The payload information includes the original volume of payload contained within the payload reservoir. The historical payload reservoir usage information is updated based on payload reservoir usage information obtained from the vape device, as described above. The application analyzes the payload information and the historical payload reservoir usage information to determine when the payload reservoir is nearly empty of payload. When this occurs, the application can alert the user to replace or order a new cartridge and/or automatically order a replacement cartridge.

In some embodiments, vape devices 10 and 100 can comprise a disposable or single-use version with reduced functionality but adapted from higher quality embodiments thereof.

In some embodiments, vape devices 10 and 100 can comprise a traditional "cigarette appearance" while other embodiments can comprise a non-cigarette appearance.

In some embodiments, vape devices 10 and 100 can comprise a light to emulate the ember of a cigarette when vapor is being inhaled.

In some embodiments, vape devices 10 and 100, in combination with application 74 running on personal computing device 72, can control the temperature and/or duty cycle of vaporization to optimize for flavor or vapor quantity for any given type of payload to be vaporized for inhalation. In some embodiments, the application 74 can be used to improve the efficiency of the operation of the vape devices 10 and 100 and to maximize the longevity of a fluid or oil-filled cartridge or payload reservoir 26 used in the vape devices.

In some embodiments, the application 74 can include features to customize a user's vape device 10 or 100, such as naming the vape device, selecting its color and controlling a vibrating device disposed in the vape device. In some embodiments, the application 74 can include security settings to control access to the vape devices 10 and 100, and to lock them when not in use.

In some embodiments, vape devices 10 and 100 can comprise a processor (i.e., such as included within microcontroller 31) operating on firmware disposed thereon. Connectivity between the vape devices 10 and 100 and the application 74 disposed on the personal computing device 72 can enable means for updating the firmware on the vape devices to keep them operating on the most current firmware. In some embodiments, the vape devices can comprise a physical configuration that can be adapted to display an OEM brand or sub-brand depending on the brand, the sales channel for the branded vape device, and the vape devices' anticipated end use such as medical, recreational, etc.

In some embodiments, vape devices 10 and 100 will be used with high quality oil products that cannot leak from the vape devices. The vape devices will avoid producing stale vapor by precise temperature control, quick cooling and providing a fast path for vapor to be inhaled from the vape devices.

In some embodiments, vape devices 10 and 100 can comprise a battery 42 as a power source for vaporizing a payload. The battery 42 can comprise a lithium ion power cell although other battery technologies can be used, as well known to those skilled in the art. As the vape devices are personal use devices, the battery 42 can comprise technology that prevents the advent of an explosion should the battery fail.

In some embodiments, vape devices 10 and 100 can be configured not to contain or use propylene glycol ("PG") or other non-essential chemicals anywhere, whether in the oils used in the vape devices or on materials used in the manufacture thereof.

In some embodiments, vape devices 10 and 100 can comprise means for preventing them from overheating.

In some embodiments, vape devices 10 and 100 can comprise means for preventing them from producing latent odors or smells. Vape devices 10 and 100 can further be configured to produce vapor that can be seen when it is exhaled by a user.

In some embodiments, vape devices 10 and 100 can be configured to enable viewing of the payload in a cartridge or payload reservoir 26 when it is inserted or attached to the vape devices. In other embodiments, the vape devices can be configured so that the payload in the cartridge is not visible when the cartridge is inserted into the vape devices.

In some embodiments, vape devices 10 and 100 can be configured to be water-resistant or water-proof.

In some embodiments, cartridges for use with the vape devices 10 and 100 can be separated from the vape devices, and can be available in various sizes in terms of the amount of payload they can contain.

In some embodiments, vape devices 10 and 100 can comprise means for acquiring data on a cartridge based on the serial number of the cartridge that can be used to control the operation of the vape device. For example, the vape device can acquire certain data specific to the payload in the cartridge to know the manufacturer-recommended temperature and/or duty cycle for heating the payload in order to achieve optimum vaporization. In some embodiments, the vape devices can comprise means for enabling the user to alter one or more operational settings of the vape devices to suit the user's personal preferences. In some embodiments, the vape devices can comprise means for tracking of data relating to the operation of the vape devices and their use by a user. In some embodiments, the vape devices can be configured to provide warnings in the advent of certain conditions of the vape devices, such as when the cartridge is almost empty, when the battery is nearly depleted, when the heating element is overheating or non-functioning to name but a few. In some embodiments, the vape devices can comprise means for monitoring and collecting data on how the vape devices are being used by a user, and to provide information and assessments about the way the user uses the vape devices in addition to being able to provide advice to the user on how to improve or optimize their use of the vape devices based on the user's current use of the vape devices.

In some embodiments, vape devices 10 and 100 can be configured for exchanging data with other personal computing devices 72 that a user may use or possess, such as a smart phone or device (like an iPhone® or Apple® Watch®) or a fitness tracking wristband (like a Fitbit®) to provide the user with further information on their life and habits.

In some embodiments, vape devices 10 and 100 can comprise means for locating them should they become lost. This can include means for communicating with a smart phone or device to provide similar functionality as the Find iPhone™ app as used on Apple® iPhones® and iPads®.

In some embodiments, vape devices 10 and 100 can be configured for communicating with an application 74 running on a smart phone or personal computing device 72, wherein the app can comprise the ability to adjust the temperature and/or duty cycle the heating element 22 operates at, as well as being able to control the operation of the vape devices for users of various experience. As an example, the application 74 can enable an anti-cough setting on the vape devices for a novice user.

Vape devices 10 and 100 can preferably communicate with smart phones or devices and operate in conjunction with applications running thereon to control and monitor the use of the vape devices by a user, as described above. In some embodiments, the application 74 can be configured to acquire specific information on the payload being vaporized based on the serial number of the cartridge. This information can then be used to control or meter the dose of vapor inhaled by the user.

In some embodiments, vape devices 10 and 100 can be locked and unlocked by the user with their personal computing device 72. In some embodiments, the vape devices can be configured to be child-resistant, as well as prevent use by an unauthorized user. In some embodiments, the vape devices can be configured to lock inherently when not connected to the application 74 for regulatory purposes. In some embodiments, the vape devices can further comprise means for identifying an authorized user when connectivity with the user's smart phone or device is lost, such as when the user does not have their smart phone or device, or when the battery in the smart phone or device becomes depleted. Such means can include a fingerprint sensor disposed on each vape device itself, wherein the vape devices can retain personal data on the user such as one or more fingerprint scan data stored in a memory on the vape devices in order to determine whether a fingerprint scan taken by the fingerprint sensor matches the fingerprint scan data stored in the memory to confirm the identity of the person attempting to use the vape devices is an authorized user.

Broadly stated, in some embodiments, vape devices 10 and 100 may comprise: an atomizer comprising a heating element, the atomizer further comprising an inlet and an outlet; a mouthpiece operatively coupled to the outlet; and a payload reservoir operatively coupled to the inlet, the payload reservoir comprising an identifier ("ID") tag comprising a unique identifier for the payload reservoir, the payload reservoir configured to hold a payload that can be drawn into the atomizer to be vaporized when the user draws on the mouthpiece.

Broadly stated, in some embodiments, the vape device can further comprise a radio frequency transceiver or wireless transceiver and at least one antenna operatively coupled to the transceiver, the combination of the transceiver and the antenna configured for enabling the wireless transmission of data between the vape device and a personal computing device.

Broadly stated, in some embodiments, an improved vape device system can be provided, the system comprising a vape device comprising: an atomizer comprising a heating element, the atomizer further comprising an inlet and an outlet, a mouthpiece operatively coupled to the outlet, a payload reservoir operatively coupled to the inlet, the payload reservoir comprising an identifier ("ID") tag comprising a unique identifier for the payload reservoir, the payload reservoir configured to hold a payload that can be drawn into the atomizer to be vaporized when the user draws on the mouthpiece, and a radio frequency transceiver and at least one antenna operatively coupled to the transceiver, the combination of the transceiver and the at least one antenna configured for wirelessly transmitting and receiving data; and a personal computing device configured for the wireless transmission of the data to and from the vape device.

Broadly stated, in some embodiments, the vape device can further comprise a switch or a draw sensor operatively coupled to the mouthpiece, the switch or the draw sensor configured to cause electrical current to flow through the heating element when the switch is operated or when the user draws on the mouthpiece.

Broadly stated, in some embodiments, the vape device can further comprise a battery configured to provide the electrical current.

Broadly stated, in some embodiments, the vape device can further comprise a battery charger configured for charging the battery.

Broadly stated, in some embodiments, the personal computing device can comprise a software application running thereon, wherein the combination of the vape device and the personal computing device can be configured for wireless control of the vape device using the personal computing device.

Broadly stated, in some embodiments, the software application can be further configured for carrying out the steps of: interpreting the ID tag via first data transmitted to the personal computing device from the vape device, the first data comprising the unique payload identifier; using the unique identifier to determine what payload is in the payload reservoir; and transmitting an operational setting to the vape device from the personal computing device, the operational setting comprising instructions to the vape device to either enable operation of the vape device if the user is authorized to use the vape device or to disable operation of the vape device if the user is not authorized to use the vape device.

Broadly stated, in some embodiments, the operational setting can further comprise instructions to the vape device to either enable operation of the vape device if the user is located in a geographic region where the payload can be vaporized by the user and to disable operation of the vape device if the user is located in a geographic region where the payload cannot be vaporized by the user.

Broadly stated, in some embodiments, the vape device can further comprise a microcontroller operatively coupled to the atomizer and to the ID tag, the microcontroller configured to control the operation of the vape device.

Broadly stated, in some embodiments, the vape device can further comprise a user interface operatively coupled to the microcontroller.

Broadly stated, in some embodiments, the user interface can comprise one or more user input control devices operatively coupled to the microcontroller, the input control devices configured for controlling the operation of the vape device when operated by the user.

Broadly stated, in some embodiments, the user interface can further comprise one or more user output indicating devices operatively coupled to the microcontroller, the output indicating devices configured for relaying information on the operation of the vape device to the user.

Broadly stated, in some embodiments, the atomizer can be disposed in an atomizer assembly; the mouthpiece and the payload reservoir can be both disposed in a mouthpiece assembly; and the microcontroller can be disposed in a control assembly, wherein the atomizer assembly can be disposed between the mouthpiece assembly and the control assembly.

Although various embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

Further, it will be understood that certain features and subcombinations are of utility and may be employed without reference to other features and subcombinations. This is contemplated by and is within the scope of the claims set forth below. In addition, the following paragraphs are provided to describe the various features and subcombinations that may be included in certain embodiments of the invention.

1. A system for authenticating users of vape devices, wherein each of the vape devices comprises a payload reservoir identified by a unique payload identifier, the system comprising: (a) a processor; (b) a memory device; and (c) a set of instructions stored in the memory device and executable by the processor to: receive user authentication information input by a user; receive a unique payload identifier for a payload reservoir of a vape device; retrieve authentication information stored in association with the unique payload identifier in a database; compare the user authentication information input by the user with the authentication information stored in the database; generate, based on the comparison, a security setting indicating whether the user who input the user authentication information is authorized to use the payload reservoir identified by the unique payload identifier; and cause transmission of the security setting to the vape device.

2. The system of claim 1, wherein the database is maintained in the memory device.

3. The system of claim 1, wherein the database is maintained in a second memory device that is located remote from the processor and the memory device.

4. The system of claim 1, wherein the processor and the memory device are located within a personal computing device, and wherein the personal computing device transmits the security setting to the vape device.

5. The system of claim 1, wherein the processor and the memory device are located within a remote server, and wherein the remote server transmits the security setting to a personal computing device which in turn transmits the security setting to the vape device.

6. The system of claim 1, wherein the set of instructions is further executable by the processor to: retrieve an operational setting stored in association with the unique payload identifier in the database; and cause transmission of the operational setting to the vape device.

7. The system of claim 1, wherein the set of instructions is further executable by the processor to: retrieve payload information stored in association with the unique payload identifier in the database, wherein the payload information comprises an identification of a substance located within the payload reservoir of the vape device; determine an operational setting associated with the substance; and cause transmission of the operational setting to the vape device.

8. The system of claim 7, wherein determining the operational setting associated with the substance comprises retrieving the operational setting stored in association with the substance in a second database.

9. The system of claim 1, wherein the set of instructions is further executable by the processor to: generate an operational setting based on at least one of user information, prescription information, location information, payload information, historical vape device usage information, and historical payload reservoir information; and cause transmission of the operational setting to the vape device.

10. The system of any of claims 6-9, wherein the operational setting comprises at least one of a duty cycle setting, a temperature setting, an operational time duration, and a dosage setting.

11. The system of any of claims 1-10, wherein the user authentication information comprises at least one of a password, a fingerprint scan, a facial recognition scan, and a retinal scan.

12. The system of any of claims 1-11, wherein operation of the vape device is prevented if the security setting indicates that the user who input the user authentication information is not authorized to use the payload reservoir identified by the unique payload identifier.

13. A method for authenticating users of vape devices, wherein each of the vape devices comprises a payload reservoir identified by a unique payload identifier, the method comprising: receiving user authentication information input by a user into a personal computing device; receiving a unique payload identifier for a payload reservoir from a vape device; retrieving authentication information stored in association with the unique payload identifier in a database; comparing the user authentication information input by the user into the personal computing device with the authentication information stored in the database; generating, based on the comparison, a security setting indicating whether the user who input the user authentication information into the personal computing device is authorized to use the payload reservoir identified by the unique payload identifier; and transmitting the security setting to the vape device.

14. The method of claim 13, further comprising: retrieving an operational setting stored in association with the unique payload identifier in the database; and transmitting the operational setting to the vape device.

15. The method of claim 13, further comprising: retrieving payload information stored in association with the unique payload identifier in the database, wherein the payload information comprises an identification of a substance located within the payload reservoir of the vape device; determining an operational setting associated with the substance; and transmitting the operational setting to the vape device.

16. The method of claim 15, wherein determining the operational setting associated with the substance comprises retrieving the operational setting stored in association with the substance in a second database.

17. The method of claim 13, further comprising: generating an operational setting based on at least one of user information, prescription information, location information, payload information, historical vape device usage information, and historical payload reservoir information; and transmitting the operational setting to the vape device.

18. The method of any of claims 14-17, wherein the operational setting comprises at least one of a duty cycle setting, a temperature setting, an operational time duration, and a dosage setting.

19. The method of any of claims 13-18, wherein the user authentication information comprises at least one of a password, a fingerprint scan, a facial recognition scan, and a retinal scan.

20. The method of any of claims 13-19, wherein operation of the vape device is prevented if the security setting indicates that the user who input the user authentication information is not authorized to use the payload reservoir identified by the unique payload identifier.

21. A system for authenticating users of vape devices, comprising: a vape device comprising a payload reservoir, wherein the vape device is configured to store a unique payload identifier that identifies the payload reservoir, and wherein the vape device is configured to transmit the unique payload identifier to a personal computing device; and an application configured to be installed on the personal computing device, wherein the application is configured to enable the personal computing device to (a) receive user authentication information input by a user, (b) receive the unique payload identifier from the vape device, (c) retrieve authentication information stored in association with the unique payload identifier in a database, (d) compare the user authentication information with the authentication information stored in the database, (e) generate, based on the comparison, a security setting indicating whether the user who input the user authentication information is authorized to use a payload reservoir identified by the unique payload identifier, and (f) transmit the security setting to the vape device.

22. The system of claim 21, wherein the database is maintained by the personal computing device.

23. The system of claim 21, wherein the database is maintained by a server that is located remote from the personal computing device.

24. The system of claim 21, wherein the application is further configured to enable the personal computing device to (g) retrieve an operational setting stored in association with the unique payload identifier in the database and (h) transmit the operational setting to the vape device.

25. The system of claim 21, wherein the application is further configured to enable the personal computing device to (g) retrieve payload information stored in association with the unique payload identifier in the database, wherein the payload information comprises an identification of a substance located within the payload reservoir, (h) determine an operational setting associated with the substance, and (i) transmit the operational setting to the vape device.

26. The system of any of claim 25, wherein determining the operational setting associated with the substance comprises retrieving the operational setting stored in association with the substance in a second database.

27. The system of claim 21, wherein the application is further configured to enable the personal computing device to (g) generate an operational setting based on at least one of user information, prescription information, location information, payload information, historical vape device usage information, and historical payload reservoir information and (h) transmit the operational setting to the vape device.

28. The system of any of claims 24-27, wherein operation of the vape device is controlled based on the operational setting.

29. The system of any of claims 24-28, wherein the operational setting comprises at least one of a duty cycle setting, a temperature setting, an operational time duration, and a dosage setting.

30. The system of any of claims 21-29, wherein the user authentication information comprises at least one of a password, a fingerprint scan, a facial recognition scan, and a retinal scan.

31. The system of any of claims 21-30, wherein operation of the vape device is prevented if the security setting indicates that the user who input the user authentication information is not authorized to use the payload reservoir identified by the unique payload identifier.

32. A system for determining whether payload reservoirs of vape devices are depleted, wherein each of the payload reservoirs is identified by a unique payload identifier, the system comprising: (a) a processor; (b) a memory device; and (c) a set of instructions stored in the memory device and executable by the processor to: receive a unique payload identifier for a payload reservoir of a vape device; retrieve payload information stored in association with the unique payload identifier in a database, wherein the payload information comprises an original volume of a payload contained within the payload reservoir; retrieve historical payload reservoir usage information stored in association with the unique payload identifier in the database; analyze the payload information stored in the database and the historical payload reservoir usage information stored in the database; generate, based on the analysis, a security setting indicating whether the payload reservoir is depleted; and cause transmission of the security setting to the vape device, wherein operation of the vape device is prevented if the security setting indicates that the payload reservoir is depleted.

33. The system of claim 32, wherein the database is maintained in the memory device.

34. The system of claim 32, wherein the database is maintained in a second memory device that is located remote from the processor and the memory device.

35. The system of claim 32, wherein the processor and the memory device are located within a personal computing device, and wherein the personal computing device transmits the security setting to the vape device.

36. The system of claim 32, wherein the processor and the memory device are located within a remote server, and wherein the remote server transmits the security setting to a personal computing device which in turn transmits the security setting to the vape device.

37. The system of claim 32, wherein the set of instructions is further executable by the processor to: receive payload reservoir usage information from the vape device; update the historical payload reservoir usage information based on the payload reservoir usage information received from the vape device; and store the updated historical payload reservoir usage information in association with the unique payload identifier in the database.

38. A method for determining whether payload reservoirs of vape devices are depleted, wherein each of the payload reservoirs is identified by a unique payload identifier, the method comprising: receiving a unique payload identifier for a payload reservoir from a vape device; retrieving payload information stored in association with the unique payload identifier in a database, wherein the payload information comprises an original volume of a payload contained within the payload reservoir; retrieving historical payload reservoir usage information stored in association with the unique payload identifier in the database; analyzing the payload information stored in the database and the historical payload reservoir usage information stored in the database; generating, based on the analysis, a security setting indicating whether the payload reservoir is depleted; and transmitting the security setting to the vape device, wherein operation of the vape device is prevented if the security setting indicates that the payload reservoir is depleted.

39. The method of claim 38, further comprising: receiving payload reservoir usage information from the vape device; updating the historical payload reservoir usage information based on the payload reservoir usage information received from the vape device; and storing the updated historical payload reservoir usage information in association with the unique payload identifier in the database.

40. A system for determining whether payload reservoirs of vape devices are depleted, comprising: a vape device comprising a payload reservoir, wherein the vape device is configured to store a unique payload identifier that identifies the payload reservoir, and wherein the vape device is configured to transmit the unique payload identifier to a personal computing device; and an application configured to be installed on the personal computing device, wherein the application is configured to enable the personal computing device to (a) receive the unique payload identifier from the vape device, (b) retrieve payload information stored in association with the unique payload identifier in a database, wherein the payload information comprises an original volume of the payload contained within the payload reservoir, (c) retrieve historical payload reservoir usage information stored in association with the unique payload identifier in the database, (d) analyze the payload information stored in the database and the historical payload reservoir usage information stored in the database, (e) generate, based on the analysis, a security setting indicating whether the payload reservoir is depleted, and (f) transmit the security setting to the vape device, wherein operation of the vape device is prevented if the security setting indicates that the payload reservoir is depleted.

41. The system of claim 40, wherein the database is maintained by the personal computing device.

42. The system of claim 40, wherein the database is maintained by a server that is located remote from the personal computing device.

43. The system of claim 40, wherein the vape device is configured to determine payload reservoir usage information based on use of the vape device and transmit the payload reservoir usage information to the personal computing device, and wherein the application is further configured to enable the personal computing device to (g) receive the payload reservoir usage information from the vape device, (h) update the historical payload reservoir usage information based on the payload reservoir usage information received from the vape device, and (i) store the updated historical payload reservoir usage information in association with the unique payload identifier in the database.

44. A system for determining whether payload reservoirs of vape devices have been returned to a return center, wherein each of the payload reservoirs is identified by a unique payload identifier, the system comprising: (a) a processor; (b) a memory device; and (c) a set of instructions stored in the memory device and executable by the processor to: receive a unique payload identifier for a payload reservoir of a vape device; determine whether the payload reservoir identified by the unique payload identifier has been returned; generate a security setting indicating whether the payload reservoir has been returned; and cause transmission of the security setting to the vape device, wherein operation of the vape device is prevented if the security setting indicates that the payload reservoir has been returned.

45. The system of claim 44, wherein the database is maintained in the memory device.

46. The system of claim 44, wherein the database is maintained in a second memory device that is located remote from the processor and the memory device.

47. The system of claim 44, wherein the processor and the memory device are located within a personal computing device, and wherein the personal computing device transmits the security setting to the vape device.

48. The system of claim 44, wherein the processor and the memory device are located within a remote server, and wherein the remote server transmits the security setting to a personal computing device which in turn transmits the security setting to the vape device.

49. A method for determining whether payload reservoirs of vape devices have been returned to a return center, wherein each of the payload reservoirs is identified by a unique payload identifier, the method comprising: receiving a unique payload identifier for a payload reservoir from a vape device; determining whether the payload reservoir identified by the unique payload identifier has been returned; generating a security setting indicating whether the payload reservoir has been returned; and transmitting the security setting to the vape device, wherein operation of the vape device is prevented if the security setting indicates that the payload reservoir has been returned.

50. A system for determining whether payload reservoirs of vape devices have been returned to a return center, comprising: a vape device comprising a payload reservoir, wherein the vape device is configured to store a unique payload identifier that identifies the payload reservoir, and wherein the vape device is configured to transmit the unique payload identifier to a personal computing device; and an application configured to be installed on the personal computing device, wherein the application is configured to enable the personal computing device to (a) receive the unique payload identifier from the vape device, (b) determine whether the payload reservoir identified by the unique payload identifier has been returned, (c) generate a security setting indicating whether the payload reservoir has been returned, and (d) transmit the security setting to the vape device, wherein operation of the vape device is prevented if the security setting indicates that the payload reservoir has been returned.

51. The system of claim 50, wherein the database is maintained by the personal computing device.

52. The system of claim 50, wherein the database is maintained by a server that is located remote from the personal computing device.

53. A system for determining whether payload reservoirs of vape devices have been recalled, wherein each of the payload reservoirs is identified by a unique payload identifier, the system comprising: (a) a processor; (b) a memory device; and (c) a set of instructions stored in the memory device and executable by the processor to: receive a unique payload identifier for a payload reservoir of a vape device; determine whether the payload reservoir identified by the unique payload identifier has been recalled; generate a security setting indicating whether the payload reservoir has been recalled; and cause transmission of the security setting to the vape device, wherein operation of the vape device is prevented if the security setting indicates that the payload reservoir has been recalled.

54. The system of claim 53, wherein the database is maintained in the memory device.

55. The system of claim 53, wherein the database is maintained in a second memory device that is located remote from the processor and the memory device.

56. The system of claim 53, wherein the processor and the memory device are located within a personal computing device, and wherein the personal computing device transmits the security setting to the vape device.

57. The system of claim 53, wherein the processor and the memory device are located within a remote server, and wherein the remote server transmits the security setting to a personal computing device which in turn transmits the security setting to the vape device.

58. The system of any of claims 53-57, wherein the vape device displays a recall message or sounds an audible recall message when the security setting indicates that the payload reservoir has been recalled.

59. A method for determining whether payload reservoirs of vape devices have been recalled, wherein each of the payload reservoirs is identified by a unique payload identifier, the method comprising: receiving a unique payload identifier for a payload reservoir from a vape device; determining whether the payload reservoir identified by the unique payload identifier has been recalled; generating a security setting indicating whether the payload reservoir has been recalled; and transmitting the security setting to the vape device, wherein operation of the vape device is prevented if the security setting indicates that the payload reservoir has been recalled.

60. The method of claim 59, further comprising displaying a recall message or sounding an audible recall message when the security setting indicates that the payload reservoir has been recalled.

61. A system for determining whether payload reservoirs of vape devices have been recalled, comprising: a vape device comprising a payload reservoir, wherein the vape device is configured to store a unique payload identifier that identifies the payload reservoir, and wherein the vape device is configured to transmit the unique payload identifier to a personal computing device; and an application configured to be installed on the personal computing device, wherein the application is configured to enable the personal computing device to (a) receive the unique payload identifier from the vape device, (b) determine whether the payload reservoir identified by the unique payload identifier has been recalled, (c) generate a security setting indicating whether the payload reservoir has been recalled, and (d) transmit the security setting to the vape device, wherein operation of the vape device is prevented if the security setting indicates that the payload reservoir has been recalled.

62. The system of claim 61, wherein the database is maintained by the personal computing device.

63. The system of claim 61, wherein the database is maintained by a server that is located remote from the personal computing device.

64. The system of any of claims 61-63, wherein one or both of the vape device and the personal computing device displays a recall message or sounds an audible recall message when the security setting indicates that the payload reservoir has been recalled.

65. A system for determining whether control assemblies are authorized for use with cartridges of vape devices, wherein each of the cartridges comprises a payload reservoir identified by a unique payload identifier, the system comprising: (a) a processor; (b) a memory device; and (c) a set of instructions stored in the memory device and executable by the processor to: receive a unique payload identifier for a payload reservoir of a vape device; receive a control assembly identifier for a control assembly of the vape device; identify a list of one or more control assembly identifiers for control assemblies that are authorized for use with the payload reservoir identified by the unique identifier; compare the control assembly identifier with the list of control assembly identifiers; generate, based on the comparison, a security setting indicating whether the control assembly identified by the control assembly identifier is authorized for use with the payload reservoir identified by the unique payload identifier; and cause transmission of the security setting to the vape device.

66. The system of claim 65, wherein the database is maintained in the memory device.

67. The system of claim 65, wherein the database is maintained in a second memory device that is located remote from the processor and the memory device.

68. The system of claim 65, wherein the processor and the memory device are located within a personal computing device, and wherein the personal computing device transmits the security setting to the vape device.

69. The system of claim 65, wherein the processor and the memory device are located within a remove server, and wherein the remote server transmits the security setting to a personal computing device which in turn transmits the security setting to the vape device.

70. The system of any of claims 65-69, wherein the control assembly identifier comprises a unique control assembly identifier.

71. The system of any of claims 65-70, wherein operation of the vape device is prevented if the security setting indicates that the control assembly identified by the control assembly identifier is not authorized for use with the payload reservoir identified by the unique payload identifier.

72. A method for determining whether control assemblies are authorized for use with cartridges of vape devices, wherein each of the cartridges comprises a payload reservoir identified by a unique payload identifier, the method comprising: receiving a unique payload identifier for a payload reservoir from a vape device; receiving a control assembly identifier for a control assembly of the vape device; identifying a list of one or more control assembly identifiers for control assemblies that are authorized for use with the payload reservoir identified by the unique identifier; comparing the control assembly identifier with the list of control assembly identifiers; generating, based on the comparison, a security setting indicating whether the control assembly identified by the control assembly identifier is authorized for use with the payload reservoir identified by the unique payload identifier; and transmitting the security setting to the vape device.

73. The method of claim 72, wherein the control assembly identifier comprises a unique control assembly identifier.

74. The method of any of claims 72-73, further comprising preventing operation of the vape device if the security setting indicates that the control assembly identified by the control assembly identifier is not authorized for use with the payload reservoir identified by the unique payload identifier.

75. A system for determining whether control assemblies are authorized for use with cartridges of vape devices, comprising: a vape device comprising a control assembly and a cartridge comprising a payload reservoir, wherein the control assembly is configured to store a control assembly identifier, wherein the cartridge is configured to store a unique payload identifier, and wherein the vape device is configured to transmit the control assembly identifier and the unique payload identifier to a personal computing device; and an application configured to be installed on the personal computing device, wherein the application is configured to enable the personal computing device to (a) receive the control assembly identifier and the unique payload identifier from the vape device, (b) identify a list of one or more control assembly identifiers for control assemblies that are authorized for use with the payload reservoir identified by the unique identifier, (c) compare the control assembly identifier with the list of control assembly identifiers, (d) generate, based on the comparison, a security setting indicating whether the control assembly identified by the control assembly identifier is authorized for use with the payload reservoir identified by the unique payload identifier, and (e) transmit the security setting to the vape device.

76. The system of claim 75, wherein the database is maintained by the personal computing device.

77. The system of claim 75, wherein the database is maintained by a server that is located remote from the personal computing device.

78. The system of any of claims 75-77, wherein the control assembly identifier comprises a unique control assembly identifier.

79. The system of any of claims 75-78, wherein operation of the vape device is prevented if the security setting indicates that the control assembly identified by the control assembly identifier is not authorized for use with the payload reservoir identified by the unique payload identifier.

Thus, while specific embodiments have been shown and discussed, various modifications may of course be made, and the invention is not limited to the specific forms or arrangement of parts and steps described herein, except insofar as such limitations are included in the following claims.

What is claimed and desired to be secured by Letters Patent is as follows:

1. A system for authorizing operation of a vape device, comprising:
   a vape device comprising a payload reservoir, wherein the vape device is configured to store a unique payload identifier that identifies and is unique to the payload reservoir, and wherein the vape device is configured to transmit the unique payload identifier to a personal computing device; and an application configured to be installed on the personal computing device, wherein the application is configured to enable the personal computing device to: confirm an identity of a user in possession of the computing device; poll the vape device for the unique payload identifier if the identity of the user is confirmed; receive the unique payload identifier from the vape device; retrieve data stored in association with the unique payload identifier in a database and utilize the data to determine whether the user is authorized to use the payload reservoir identified by the unique payload identifier; generate a security setting indicating whether the user is authorized to use the payload reservoir; and transmit the security setting to the vape device.

2. The system of claim 1, wherein the identity of the user is confirmed when: (i) the user unlocks the personal computing device; and (ii) the user accesses the application on the personal computing device.

3. The system of claim 2, wherein the user unlocks the personal computing device by inputting user authentication information associated with a security feature of the personal computing device, wherein the user authentication information comprises at least one of a password, a fingerprint scan, a facial recognition scan, and a retinal scan.

4. The system of claim 2, wherein the user accesses the application on the personal computing device by opening the application.

5. The system of claim 2, wherein the user accesses the application on the personal computing device by opening the application and inputting user authentication information associated with a security feature of the application, wherein the user authentication information comprises at least one of a password, a fingerprint scan, a facial recognition scan, and a retinal scan.

6. The system of claim 1, wherein the data comprises at least one of user information, prescription information, payload information, historical vape device usage information, and historical payload reservoir information.

7. The system of claim 6, wherein the application is configured to enable the personal computing device to: retrieve location information associated with the personal computing device; and utilize the location information to determine whether the user is authorized to use the payload reservoir.

8. The system of claim 1, wherein the database is maintained in one of: (a) a first memory device of the personal computing device or (b) a second memory device that is located remote from the personal computing device.

9. The system of claim 1, wherein the vape device is configured to prevent operation of the vape device if the security setting indicates that the user is not authorized to use the payload reservoir.

10. The system of claim 1, wherein the application is configured to enable the personal computing device to: utilize the unique payload identifier to determine an operational setting for the vape device; and transmit the operational setting to the vape device.

11. The system of claim 10, wherein the operational setting comprises at least one of a duty cycle setting, a temperature setting, an operational time duration, and a dosage setting.

12. The system of claim 10, wherein the security setting is transmitted within the operational setting to the vape device.

13. The system of claim 1, wherein the application is configured to enable the personal computing device to: retrieve an operational setting stored in association with the unique payload identifier in a database; and transmit the operational setting to the vape device.

14. The system of claim 1, wherein the application is configured to enable the personal computing device to: retrieve payload information stored in association with the unique payload identifier in a database, wherein the payload information comprises an identification of a substance located within the payload reservoir of the vape device; determine an operational setting associated with the substance; and transmit the operational setting to the vape device.

15. The system of claim 14, wherein determining the operational setting associated with the substance comprises retrieving the operational setting stored in association with the substance in a second database.

16. The system of claim 1, wherein the data comprises at least one of user information, prescription information, payload information, historical vape device usage information, and historical payload reservoir information; and wherein the application is configured to enable the personal computing device to: utilize the data to determine an operational setting for the vape device; and transmit the operational setting to the vape device.

17. A method for authorizing operation of a vape device, wherein the vape device comprises a payload reservoir identified by a unique payload identifier, the method comprising:
confirming an identity of a user in possession f a personal computing device;
polling the vape device for the unique payload identifier if the identity of the user is confirmed, wherein the unique payload identifier identifies and is unique to the payload reservoir;
receiving the unique payload identifier from the vape device;
retrieving data stored in association with the unique payload identifier in a database and utilizing the data to determine whether the user is authorized to use the payload reservoir identified by the unique payload identifier;
generating a security setting indicating whether the user is authorized to use the payload reservoir; and
transmitting the security setting to the vape device.

18. The method of claim 17, wherein the identity of the user is confirmed when: (i) the user unlocks the personal computing device; and (ii) the user accesses an application on the personal computing device.

19. The method of claim 18, wherein the user unlocks the personal computing device by inputting user authentication information associated with a security feature of the personal computing device, wherein the user authentication information comprises at least one of a password, a fingerprint scan, a facial recognition scan, and a retinal scan.

20. The method of claim 18, wherein the user accesses the application on the personal computing device by opening the application.

21. The method of claim 18, wherein the user accesses the application on the personal computing device by opening the application and inputting user authentication information associated with a security feature of the application, wherein the user authentication information comprises at least one of a password, a fingerprint scan, a facial recognition scan, and a retinal scan.

22. The method of claim 17, further comprising:
retrieving secondary data stored in association with the unique payload identifier in a database, wherein the secondary data comprises at least one of user information, prescription information, payload information, historical vape device usage information, and historical payload reservoir information; and utilizing the secondary data to determine whether the user is authorized to use the payload reservoir.

23. The method of claim 22, further comprising:
retrieving location information associated with the personal computing device; and
utilizing the location information to determine whether the user is authorized to use the payload reservoir.

24. The method of claim 22, wherein the database is maintained in one of: (a) a first memory device of the personal computing device or (b) a second memory device that is located remote from the personal computing device.

25. The method of claim 17, wherein the vape device is configured to prevent operation of the vape device if the security setting indicates that the user is not authorized to use the payload reservoir.

26. The method of claim 17, further comprising:
utilizing the unique payload identifier to determine an operational setting for the vape device; and
transmitting the operational setting to the vape device.

27. The method of claim 26, wherein the operational setting comprises at least one of a duty cycle setting, a temperature setting, an operational time duration, and a dosage setting.

28. The method of claim 26, wherein the security setting is transmitted within the operational setting to the vape device.

29. The method of claim 17, further comprising:
retrieving an operational setting stored in association with the unique payload identifier in a database; and
transmitting the operational setting to the vape device.

30. The method of claim 17, further comprising:
retrieving payload information stored in association with the unique payload identifier in a database, wherein the payload information comprises an identification of a substance located within the payload reservoir of the vape device;
determining an operational setting associated with the substance; and
transmitting the operational setting to the vape device.

31. The method of claim 30, wherein the step of determining the operational setting associated with the substance comprises:
retrieving the operational setting stored in association with the substance in a second database.

32. The method of claim 17, further comprising:
retrieving secondary data stored in association with the unique payload identifier in a database, wherein the secondary data comprises at least one of user information, prescription information, payload information, historical vape device usage information, and historical payload reservoir information;
utilizing the secondary data to determine an operational setting for the vape device; and
transmitting the operational setting to the vape device.

33. A system for authorizing operation of a vape device by a user, comprising:

a vape device comprising a payload reservoir, wherein the vape device is configured to store a unique payload identifier that identifies and is unique to the payload reservoir, and wherein the vape device is configured to transmit the unique payload identifier to a personal computing device; and an application configured to be installed on the personal computing device, wherein the application is configured to enable the personal computing device to:
receive the unique payload identifier from the vape device;
retrieve secondary data stored in association with the unique payload identifier in a database, wherein the secondary data comprises at least one of user information, prescription information, payload information, historical vape device usage information, and historical payload reservoir information;
utilize the secondary data to (i) determine whether the user is authorized to use the payload reservoir identified by the unique payload identifier and (ii) determine an operational setting for the vape device;
generate a security setting indicating whether the user is authorized to use the payload reservoir; and
transmit the security setting with the operational setting to the vape device.

34. The system of claim 33, wherein the application is configured to enable the personal computing device to: confirm an identity of the user; and poll the vape device for the unique payload identifier if the identity of the user is confirmed.

35. The system of claim 34, wherein the identity of the user is confirmed when: (i) the user unlocks the personal computing device; and (ii) the user accesses the application on the personal computing device.

36. The system of claim 35, wherein the user unlocks the personal computing device by inputting user authentication information associated with a security feature of the personal computing device, wherein the user authentication information comprises at least one of a password, a fingerprint scan, a facial recognition scan, and a retinal scan.

37. The system of claim 35, wherein the user accesses the application on the personal computing device by opening the application.

38. The system of claim 35, wherein the user accesses the application on the personal computing device by opening the application and inputting user authentication information associated with a security feature of the application, wherein the user authentication information comprises at least one of a password, a fingerprint scan, a facial recognition scan, and a retinal scan.

39. The system of claim 33, wherein the application is configured to enable the personal computing device to: retrieve location information associated with the personal computing device; and utilize the location information to determine whether the user is authorized to use the payload reservoir.

* * * * *

UNITED STATES PATENT AND TRADEMARK OFFICE
CERTIFICATE OF CORRECTION

PATENT NO. : 11,106,773 B2
APPLICATION NO. : 16/419593
DATED : August 31, 2021
INVENTOR(S) : Peter Popplewell, Andrew Stewart and Steven Penney Page 1 of 1

It is certified that error appears in the above-identified patent and that said Letters Patent is hereby corrected as shown below:

In the Claims

Column 40
Line 28, delete "f" between "possession" and "a" and replace it with "of" therefor.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*